(12) United States Patent
Akino et al.

(10) Patent No.: US 9,705,097 B2
(45) Date of Patent: Jul. 11, 2017

(54) METAL COMPLEX AND LIGHT-EMITTING DEVICE CONTAINING THE METAL COMPLEX

(71) Applicants: Sumitomo Chemical Company, Limited, Tokyo (JP); National Institute of Advanced Industrial Science and Technology, Tokyo (JP)

(72) Inventors: Nobuhiko Akino, Ibaraki (JP); Taichi Abe, Ibaraki (JP); Hideo Konno, Ibaraki (JP); Shigeru Shimada, Ibaraki (JP); Kazuhiko Sato, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 350 days.

(21) Appl. No.: 14/372,033

(22) PCT Filed: Jan. 10, 2013

(86) PCT No.: PCT/JP2013/050268
§ 371 (c)(1),
(2) Date: Jul. 14, 2014

(87) PCT Pub. No.: WO2013/108700
PCT Pub. Date: Jul. 25, 2013

(65) Prior Publication Data
US 2014/0374727 A1    Dec. 25, 2014

(30) Foreign Application Priority Data
Jan. 18, 2012 (JP) .................................. 2012-008188

(51) Int. Cl.
*H01L 51/54* (2006.01)
*C09K 11/06* (2006.01)
(Continued)

(52) U.S. Cl.
CPC ........ *H01L 51/0085* (2013.01); *C07F 7/0809* (2013.01); *C07F 15/0033* (2013.01); *C08K 5/0091* (2013.01); *C08K 5/56* (2013.01); *C09K 11/06* (2013.01); *H01L 51/5012* (2013.01); *H05B 33/10* (2013.01); *C09K 2211/1007* (2013.01); *C09K 2211/1059* (2013.01); *C09K 2211/185* (2013.01); *H01L 51/5016* (2013.01); *H01L 51/5203* (2013.01)

(58) Field of Classification Search
None
See application file for complete search history.

(56) References Cited

U.S. PATENT DOCUMENTS 7,659,010 B2  2/2010 Burn et al.
8,216,699 B2  7/2012 Burn et al.
(Continued)

FOREIGN PATENT DOCUMENTS

CN   1791655 A       6/2006
JP   2007-504272 A   3/2007
(Continued)

OTHER PUBLICATIONS

Lo et al., "High-Triplet-Energy Dendrons: Enhancing the Luminescence of Deep Blue Phosphorescent Iridium(III) Complexes", J. AM. Chem. Soc., vol. 131, No. 46, pp. 16681-16688 (2009).
(Continued)

*Primary Examiner* — Marie R. Yamnitzky
(74) *Attorney, Agent, or Firm* — Panitch Schwarze Bellisario & Nadel LLP

(57) ABSTRACT

A highly stable metal complex useful for the manufacture of a light-emitting device has an excellent lifetime property, particularly in a blue region, specifically a metal complex represented by Formula (1):

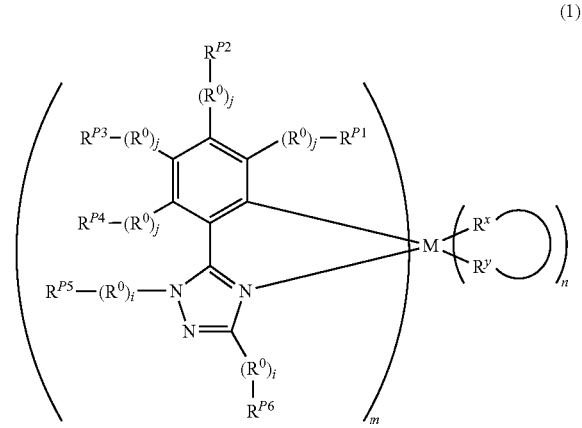

(1)

wherein M is a metal atom; each $R^0$ independently represents a divalent linking group; i and j each independently represent 0 or 1; $R^{P1}$, $R^{P2}$, $R^{P3}$, $R^{P4}$, $R^{P5}$ and $R^{P6}$ each independently represent a hydrogen atom and the like, with a proviso that at least one of $R^{P1}$, $R^{P2}$, $R^{P3}$, $R^{P4}$, $R^{P5}$ and $R^{P6}$ is a dendron; m is an integer of from 1 to 3, n is an integer of from 0 to 2, and m+n is 2 or 3; and the portion represented by Formula (2):

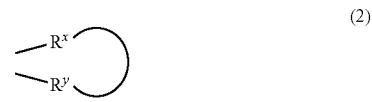

(2)

represents a bidentate ligand; wherein $R^x$ and $R^y$ are an atom bonding to the metal atom M, and each independently represents a carbon atom and the like.

14 Claims, No Drawings

(51) Int. Cl.
*H01L 51/00* (2006.01)
*C07F 15/00* (2006.01)
*C07F 7/08* (2006.01)
*C08K 5/00* (2006.01)
*H05B 33/10* (2006.01)
*H01L 51/50* (2006.01)
*C08K 5/56* (2006.01)
*H01L 51/52* (2006.01)

(56) References Cited

U.S. PATENT DOCUMENTS

| | | | |
|---|---|---|---|
| 2006/0000867 A1 | 1/2006 | Shelton et al. | |
| 2006/0008670 A1 | 1/2006 | Lin et al. | |
| 2006/0251923 A1 | 11/2006 | Lin et al. | |
| 2007/0009759 A1 | 1/2007 | Burn et al. | |
| 2008/0038586 A1 | 2/2008 | Nishizeki et al. | |
| 2009/0102370 A1* | 4/2009 | Taka et al. | C07D 233/58 313/504 |
| 2013/0087820 A1 | 4/2013 | Zhu et al. | |
| 2013/0285035 A1 | 10/2013 | Taka et al. | |

FOREIGN PATENT DOCUMENTS

| | | |
|---|---|---|
| JP | 2012-151266 A | 8/2012 |
| JP | 2013-041990 A | 2/2013 |
| JP | 2013147551 A | 8/2013 |
| WO | 0215645 A1 | 2/2002 |
| WO | 2004101707 A1 | 11/2004 |
| WO | 2012070596 A1 | 5/2012 |
| WO | 2013191086 A1 | 12/2013 |
| WO | 2013191088 A1 | 12/2013 |

OTHER PUBLICATIONS

Office Action issued Jun. 3, 2016 in CN Application No. 201380005631.6.

Office Action issued Sep. 30, 2015 in CN Application No. 201380005631.6.

Office Action issued Dec. 8, 2015 in JP Application No. 2012008188.

Int'l Search Report issued Apr. 2, 2013 in Int'l Application No. PCT/JP2013/050268.

Lo et al, "Solution-Processible Phosphorescent Blue Dendrimers Based on Biphenyl-Dendrons and Fac-tris (phenyltriazolyl)iridium(III) Cores," Advanced Functional Materials, vol. 18, pp. 3080-3090 (2008).

Levell et al, "Efficient Phosphorescence by Reducing Intrachain Chromophore Interactions in Dendrimer-Containing Polymers," The Journal of Physical Chemistry, vol. 115, pp. 25464-25469 (2011).

Lai et al, "A Phosphorescent Poly(dendrimer) Containing Iridium(III) Complexes: Synthesis and Light-Emitting Properties," Macromolecules, vol. 43, pp. 6986-6994 (2010).

* cited by examiner

METAL COMPLEX AND LIGHT-EMITTING DEVICE CONTAINING THE METAL COMPLEX

CROSS-REFERENCE TO RELATED APPLICATION

This application is a Section 371 of International Application No. PCT/JP2013/050268, filed Jan. 10, 2013, which was published in the Japanese language on Jul. 25, 2013, under International Publication No. WO 2013/108700 A1, and the disclosure of which is incorporated herein by reference.

TECHNICAL FIELD

The present invention relates to a metal complex and a light-emitting device containing the metal complex.

BACKGROUND ART

For light-emitting materials used for a light-emitting layer of an organic electroluminescent device (hereinafter may be referred to as a "light-emitting device"), metal complexes exhibiting light emission from a triplet excited state can be expected to have a higher luminous efficiency than fluorescent materials exhibiting light emission from a singlet excited state. As a blue light-emitting metal complex exhibiting light emission from a triplet excited state (phosphorescent light emission), there are known, for example, FIrpic which is a metal complex having an iridium atom as a metal atom (Patent Document 1) and a metal complex having a triazole ring-containing ligand (Patent Document 2).

RELATED ART DOCUMENT

Patent Document

Patent Document 1: WO 2002/15645
Patent Document 2: WO 2004/101707

SUMMARY OF THE INVENTION

Problem to be Solved by the Invention

For practical use of an organic electroluminescent device using metal complexes, it is desired to develop a metal complex which is useful for the manufacture of a light-emitting device having an excellent luminous efficiency, lifetime property and the like in three primary colors of red, green and blue. It is desired to develop a highly stable metal complex useful for the manufacture of a light-emitting device having an excellent lifetime property, particularly in a blue region in comparison with red and green.

Thus, an object of the present invention is to provide a highly stable metal complex useful for the manufacture of a light-emitting device having an excellent lifetime property, particularly in a blue region. It is also an object of the present invention to provide a light-emitting device using the metal complex.

Means for Solving Problem

Firstly, the present invention provides a metal complex represented by Formula (1):

[Chem. 1]

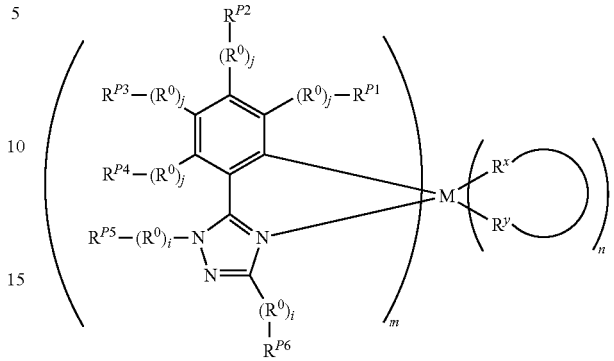

(1)

wherein
M is a metal atom selected from the group consisting of a ruthenium atom, a rhodium atom, a palladium atom, an osmium atom, an iridium atom and a platinum atom;
each $R^0$ is independently a divalent linking group selected from the group consisting of a group represented by Formula (L-1), a group represented by Formula (L-2) and a group represented by Formula (L-3):

[Chem. 2]

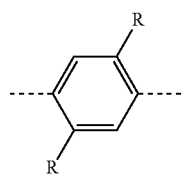

(L-1)

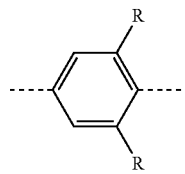

(L-2)

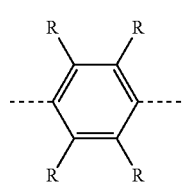

(L-3)

wherein each R independently represents an alkyl group;
each i independently represents 0 or 1;
each j independently represents 0 or 1;
$R^{P1}$, $R^{P2}$, $R^{P3}$, $R^{P4}$, $R^{P5}$ and $R^{P6}$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, and $R^{P1}$ and $R^{P2}$ may be connected to form a ring structure, $R^{P2}$ and $R^{P3}$ may be connected to form a ring structure, and $R^{P3}$ and $R^{P4}$ may be connected to form a ring structure, with a proviso that at least one of $R^{P1}$, $R^{P2}$, $R^{P3}$, $R^{P4}$, $R^{P5}$ and $R^{P6}$ is a dendron, and when $R^{P1}$, $R^{P2}$, $R^{P3}$ or $R^{P4}$ is the dendron, j which represents the number of the linking group $R^0$ linking to the dendron is 1;

m is an integer of from 1 to 3, n is an integer of from 0 to 2, and m+n is 2 or 3; and the portion represented by Formula (2):

[Chem. 3]

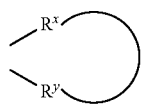

(2)

represents a bidentate ligand;

wherein $R^x$ and $R^y$ are an atom bonding to the metal atom M, and each independently represent a carbon atom, an oxygen atom or a nitrogen atom.

Secondly, the present invention provides a composition comprising the metal complex and a charge transport compound.

Thirdly, the present invention provides a composition comprising the metal complex and a solvent or dispersion medium.

Fourthly, the present invention provides a film containing the metal complex.

Fifthly, the present invention provides a light-emitting device that includes (is equipped with) electrodes composed of an anode and a cathode, and a layer containing the metal complex provided between the electrodes.

Sixthly, the present invention provides a planar light source and illumination apparatus that include (are equipped with) the light-emitting device.

Effect of Invention

The metal complex of the present invention has excellent stability. The metal complex of the present invention is therefore particularly useful for the manufacture of a light-emitting device.

EMBODIMENTS FOR CARRYING OUT THE INVENTION

The present invention will be described in detail below.
<Metal Complex>

The metal complex of the present invention is described.

The metal complex of the present invention is a metal complex having m ligand(s) containing a phenyl ring and a triazole ring, specifically, a metal complex represented by Formula (1).

The metal complex represented by Formula (1) contains ligand(s) the number of which is defined by the subscript m and bidentate ligand(s) represented by Formula (2) the number of which is defined by a subscript n. Hereinafter, a simple expression "ligand" means both the ligand the number of which is defined by the subscript m and the bidentate ligand the number of which is defined by the subscript n.

In Formula (1), m is an integer of from 1 to 3, and n is an integer of from 0 to 2, preferably n is 0 or 1, and more preferably n is 0. However, m+n, the total number of ligands which can be bonded to the metal atom M, meets the valence of the metal atom M. For example, when the metal atom is an iridium atom, m is 1, 2 or 3, n is 0, 1 or 2, and m+n is 3. Preferably, m=3 and n=0, or m=2 and n=1, and more preferably, m=3 and n=0. The metal atom M can be coordinately bonded to a nitrogen atom of the triazole ring and can be covalently bonded to a carbon atom of the benzene ring. The solid lines extending from M indicate such bonds (the same shall apply hereinafter).

The metal complex represented by Formula (1) is preferably a metal complex represented by Formula (3) below (that is, n=0):

[Chem. 4]

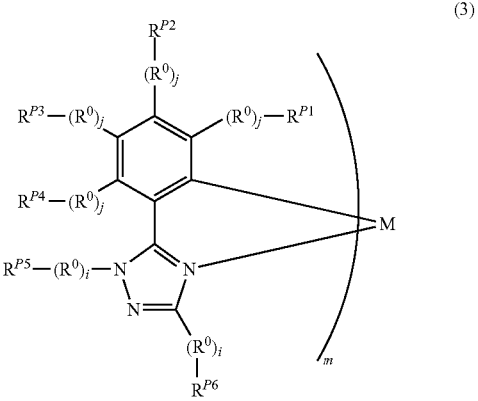

(3)

wherein M, $R^0$, $R^{P1}$, $R^{P2}$, $R^{P3}$, $R^{P4}$, $R^{P5}$, $R^{P6}$, i, j and m represent the same meaning as above.

In the metal complex of the present invention, $R^{P1}$, $R^{P2}$, $R^{P3}$, $R^{P4}$, $R^{P5}$ and $R^{P6}$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group. $R^{P1}$ and $R^{P2}$ may be connected to form a ring structure, $R^{P2}$ and $R^{P3}$ may be connected to form a ring structure, and $R^{P3}$ and $R^{P4}$ may be connected to form a ring structure. However, at least one of $R^{P1}$, $R^{P2}$, $R^{P3}$, $R^{P4}$, $R^{P5}$ and $R^{P6}$ is a dendron described below, and when $R^{P1}$, $R^{P2}$, $R^{P3}$ or $R^{P4}$ is the dendron, j which represents the number of the linking group $R^0$ linking to the dendron is 1.

Preferably, $R^{P1}$, $R^{P2}$, $R^{P3}$, $R^{P4}$, $R^{P5}$ and $R^{P6}$ each independently represent a halogen atom, an alkyl group, an alkyloxy group, an aryl group or a monovalent heterocyclic group, and more preferably at least one of $R^{P1}$, $R^{P2}$, $R^{P3}$, $R^{P4}$, $R^{P5}$ and $R^{P6}$ is a halogen atom, an alkyl group, an alkyloxy group, an aryl group or a monovalent heterocyclic group.

In the metal complex of the present invention, at least one of $R^{P1}$, $R^{P2}$, $R^{P3}$, $R^{P4}$, $R^{P5}$ and $R^{P6}$ is a dendron for the purpose of achieving at least one of: enhancing the solubility; enhancing the application and film formation properties; and introducing further functionalities (for example, charge transport property).

The dendron is a group having a branching structure, and makes it possible to impart various functions to the metal complex. A highly branched large molecule having dendrons may be referred to as a dendrimer. Such molecule is described in, for example, WO02/066575, WO02/066552 and WO02/067343, and is designed and synthesized for the purpose of imparting various functions to the metal complex.

Specifically, the dendron is a group having a branching structure attributed to a substituent that the group has. The dendron is preferably an aryl group having two or more substituents or a monovalent heterocyclic group having two or more substituents, more preferably an aryl group having two or more substituents, and further preferably a phenyl group having two or more substituents. As a substituent that an aryl group, a monovalent heterocyclic group or a phenyl group as the dendron has, preferred is an alkyl group or an alkyloxy group, and more preferred is an alkyl group. The details of the aryl group and the monovalent heterocyclic group are described below. The details of the substituent that an aryl group, a monovalent heterocyclic group or a phenyl group as the dendron has are also described below.

In the metal complex of the present invention, a ligand is substituted with one or more dendron. The substitution position of the dendron on the phenyl ring in the ligand may be any of $R^{P1}$, $R^{P2}$, $R^{P3}$ and $R^{P4}$ and the substitution position is preferably $R^{P2}$ or $R^{P3}$, and further preferably $R^{P3}$. The substitution position of the dendron on the triazole ring in the ligand may be any of $R^{P5}$ and $R^{P6}$, and the substitution position is preferably $R^{P5}$. As the metal complex, preferred is a metal complex represented by Formula (3-1) wherein $R^{P5}$ is a dendron and a metal complex represented by Formula (3-2) wherein $R^{P3}$ is a dendron, and more preferred is a metal complex wherein $R^{P3}$ and $R^{P5}$ are dendrons.

[Chem. 5]

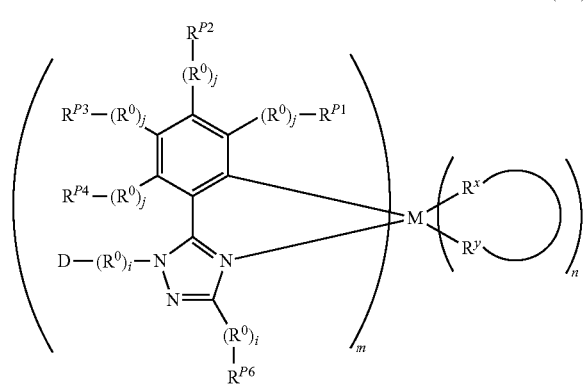

(3-1)

In the formula, M, $R^0$, $R^1$, $R^2$, $R^{P3}$, $R^{P4}$, $R^{P6}$ the portion represented by Formula (2), $R^x$, $R^y$, i, j, m and n represent the same meaning as above, and D represents the dendron.

[Chem. 6]

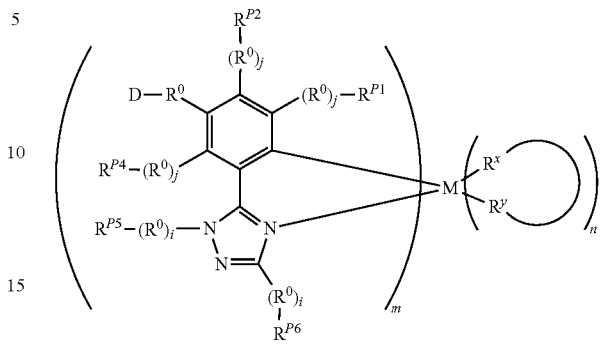

(3-2)

In the formula, M, $R^0$, $R^{P1}$, $R^{P2}$, $R^{P4}$, $R^{P5}$, $R^{P6}$, the portion represented by Formula (2), $R^x$, $R^y$, i, j, m and n represent the same meaning as above, and D represents the dendron.

Although a peak wavelength of emission spectrum of the metal complex of the present invention is not limited, it is preferably from 430 nm to 630 nm, more preferably from 430 nm to 580 nm, further preferably from 430 nm to 530 nm, and particularly preferably from 430 nm to 510 nm.

The peak of emission spectrum of the metal complex of the present invention can be evaluated, for example, by dissolving the metal complex in an organic solvent such as xylene, toluene, chloroform and tetrahydrofuran to prepare a dilute solution (the concentration of the metal complex in the organic solvent is in a range of, for example, from $1 \times 10^{-6}$ to $1 \times 10^{-7}$ mol/L), and measuring a PL spectrum of the dilute solution.

The metal atom M to be the metal atom of the metal complex of the present invention is a metal atom selected from the group consisting of a ruthenium atom, a rhodium atom, a palladium atom, an osmium atom, an iridium atom and a platinum atom. These metal atoms involve spin-orbit interaction in the metal complex and can produce an intersystem crossing between a singlet state and a triplet state. The metal atom M is preferably an osmium atom, an iridium atom or a platinum atom, further preferably an iridium atom or a platinum atom, and particularly preferably an iridium atom.

$R^0$ is a divalent linking group between the ligand and the group represented by $R^{P1}$, $R^{P2}$, $R^{P3}$, $R^{P4}$, $R^{P5}$ and $R^{P6}$, and each $R^0$ is independently selected from a group represented by Formula (L-1), a group represented by Formula (L-2), and a group represented by Formula (L-3). The divalent linking group is preferably a group represented by Formula (L-1) or a group represented by Formula (L-2), and more preferably a group represented by Formula (L-2).

j, which represents the number of the linking group $R^0$, is each 0 or 1. When $R^{P1}$, $R^{P2}$, $R^{P3}$ or $R^{P4}$ is the dendron, j which represents the number of the linking group $R^0$ linking to the dendron is 1. j, which represents the number of the linking group $R^0$, is preferably 1.

In Formulae (L-1), (L-2) and (L-3), R represents an alkyl group. The alkyl group may be any of linear, branched and cyclic, and is preferably linear or branched, and more preferably linear. The linear alkyl group has usually 1 to 10 carbon atoms, preferably 1 to 6 carbon atoms, more preferably 1 to 3 carbon atoms, and further preferably 1 carbon atom. The branched and cyclic alkyl groups have usually 3 to 10 carbon atoms, and preferably 3 to 6 carbon atoms.

The halogen atom represented by $R^{P1}$, $R^{P2}$, $R^{P3}$, $R^{P4}$, $R^{P5}$ and $R^{P6}$ includes a fluorine atom, a chlorine atom, a bromine atom and an iodine atom, and the halogen atom is preferably a fluorine atom.

The alkyl group represented by $R^{P1}$, $R^{P2}$, $R^{P3}$, $R^{P4}$, $R^{P5}$ and $R^{P6}$ may be any of linear, branched and cyclic. The linear alkyl group has usually 1 to 12 carbon atoms, and preferably 3 to 10 carbon atoms. The branched and cyclic alkyl groups have usually 3 to 12 carbon atoms, and preferably 3 to 10 carbon atoms. The alkyl group may have a substituent. The number of carbon atoms described above does not include the number of carbon atoms of the substituent.

Examples of such alkyl group include a methyl group, an ethyl group, a propyl group, an iso-propyl group, a butyl group, an iso-butyl group, a tert-butyl group, a pentyl group, a hexyl group, a cyclohexyl group, a heptyl group, an octyl group, a 2-ethylhexyl group, a nonyl group, a decyl group, a 3,7-dimethyloctyl group, a lauryl group, a trifluoromethyl group, a pentafluoroethyl group, a perfluorobutyl group, a perfluorohexyl group and a perfluorooctyl group. Among them, a pentyl group, a hexyl group, an octyl group, a 2-ethylhexyl group, a decyl group and a 3,7-dimethyloctyl group are preferred.

The alkyloxy group represented by $R^{P1}$, $R^{P2}$, $R^{P3}$, $R^{P4}$, $R^{P5}$ and $R^{P6}$ may be any of linear, branched and cyclic. The linear alkyloxy group has usually 1 to 12 carbon atoms, and preferably 3 to 10 carbon atoms. The branched and cyclic alkyloxy groups have usually 3 to 12 carbon atoms, and preferably 3 to 10 carbon atoms. The alkyloxy group may have a substituent. The number of carbon atoms described above does not include the number of carbon atoms of the substituent.

Examples of such alkyloxy group include a methyloxy group, an ethyloxy group, a propyloxy group, an iso-propyloxy group, a butyloxy group, an iso-butyloxy group, a tert-butyloxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauryloxy group, a trifluoromethyloxy group, a pentafluoroethyloxy group, a perfluorobutyloxy group, a perfluorohexyloxy group, a perfluorooctyloxy group, a methyloxymethyloxy group and a 2-methyloxyethyloxy group. Among them, a pentyloxy group, a hexyloxy group, an octyloxy group, a 2-ethylhexyloxy group, a decyloxy group and a 3,7-dimethyloctyloxy group are preferred.

The alkylthio group represented by $R^{P1}$, $R^{P2}$, $R^{P3}$, $R^{P4}$, $R^{P5}$ and $R^{P6}$ may be any of linear, branched and cyclic. The linear alkylthio group has usually 1 to 12 carbon atoms, and preferably 3 to 10 carbon atoms. The branched and cyclic alkylthio groups have usually 3 to 12 carbon atoms, and preferably 3 to 10 carbon atoms. The alkylthio group may have a substituent. The number of carbon atoms described above does not include the number of carbon atoms of the substituent.

Examples of such alkylthio group include a methylthio group, an ethylthio group, a propylthio group, an iso-propylthio group, a butylthio group, an iso-butylthio group, a tert-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group and a trifluoromethylthio group. Among them, a pentylthio group, a hexylthio group, an octylthio group, a 2-ethylhexylthio group, a decylthio group and a 3,7-dimethyloctylthio group are preferred.

The aryl group represented by $R^{P1}$, $R^{P2}$, $R^{P3}$, $R^{P4}$, $R^{P5}$ and $R^{P6}$ has usually 6 to 60 carbon atoms, and preferably 7 to 48 carbon atoms. The aryl group may have a substituent. The number of carbon atoms described above does not include the number of carbon atoms of the substituent.

Examples of such aryl group include a phenyl group, a $C_1$ to $C_{12}$ alkyloxyphenyl group ("$C_1$ to $C_{12}$ alkyloxy" means that the alkyloxy moiety has 1 to 12 carbon atoms, and the same shall apply hereinafter), a $C_1$ to $C_{12}$ alkylphenyl group ("$C_1$ to $C_{12}$ alkyl" means that the alkyl moiety has 1 to 12 carbon atoms, and the same shall apply hereinafter), a 1-naphthyl group, a 2-naphthyl group, a 1-anthracenyl group, a 2-anthracenyl group, a 9-anthracenyl group and a pentafluorophenyl group. Among them, a $C_1$ to $C_{12}$ alkyloxyphenyl group and a $C_1$ to $C_{12}$ alkylphenyl group are preferred. Here, the aryl group is an atomic group remaining after removing one hydrogen atom from an aromatic hydrocarbon. The aromatic hydrocarbon includes a compound having a fused ring and a compound in which two or more selected from among an independent benzene ring and/or a fused ring are bonded with each other either directly or through a group such as a vinylene group.

The above $C_1$ to $C_{12}$ alkyl is alkyl having 1 to 12 carbon atoms, and is the same as described and exemplified above in regard to the alkyl group. Accordingly, examples of $C_1$ to $C_{12}$ alkyloxy in the group include methyloxy, ethyloxy, propyloxy, iso-propyloxy, butyloxy, iso-butyloxy, tert-butyloxy, pentyloxy, hexyloxy, cyclohexyloxy, heptyloxy, octyloxy, 2-ethylhexyloxy, nonyloxy, decyloxy, 3,7-dimethyloctyloxy and lauryloxy. Examples of $C_1$ to $C_{12}$ alkylphenyl in the group include methylphenyl, ethylphenyl, dimethylphenyl, propylphenyl, mesityl, methylethylphenyl, iso-propylphenyl, butylphenyl, iso-butylphenyl, tert-butylphenyl, pentylphenyl, isoamylphenyl, hexylphenyl, heptylphenyl, octylphenyl, nonylphenyl, decylphenyl and dodecylphenyl. The same shall apply hereinafter.

The aryloxy group represented by $R^{P1}$, $R^{P2}$, $R^{P3}$, $R^{P4}$, $R^{P5}$ and $R^{P6}$ has usually 6 to 60 carbon atoms, and preferably 7 to 48 carbon atoms. The aryloxy group may have a substituent. The number of carbon atoms described above does not include the number of carbon atoms of the substituent.

Examples of such aryloxy group include a phenyloxy group, a $C_1$ to $C_{12}$ alkyloxyphenyloxy group, a $C_1$ to $C_{12}$ alkylphenyloxy group, a 1-naphthyloxy group, a 2-naphthyloxy group and a pentafluorophenyloxy group. Among them, a $C_1$ to $C_{12}$ alkyloxyphenyloxy group and a $C_1$ to $C_{12}$ alkylphenyloxy group are preferred.

The arylthio group represented by $R^{P1}$, $R^{P2}$, $R^{P3}$, $R^{P4}$, $R^{P5}$ and $R^{P6}$ has usually 6 to 60 carbon atoms, and preferably 7 to 48 carbon atoms. The arylthio group may have a substituent. The number of carbon atoms described above does not include the number of carbon atoms of the substituent.

Examples of such arylthio group include a phenylthio group, a $C_1$ to $C_{12}$ alkyloxyphenylthio group, a $C_1$ to $C_{12}$ alkylphenylthio group, a 1-naphthylthio group, a 2-naphthylthio group and a pentafluorophenylthio group. Among them, a $C_1$ to $C_{12}$ alkyloxyphenylthio group and a $C_1$ to $C_{12}$ alkylphenylthio group are preferred.

The arylalkyl group represented by $R^{P1}$, $R^{P2}$, $R^{P3}$, $R^{P4}$, $R^{P5}$ and $R^{P6}$ has usually 7 to 60 carbon atoms, and preferably 7 to 48 carbon atoms. The arylalkyl group may have a substituent. The number of carbon atoms described above does not include the number of carbon atoms of the substituent.

Examples of such arylalkyl group include a phenyl-$C_1$ to $C_{12}$ alkyl group, a $C_1$ to $C_{12}$ alkyloxypheny-$C_1$ to $C_{12}$ alkyl group, a $C_1$ to $C_{12}$ alkylphenyl-$C_1$ to $C_{12}$ alkyl group, a 1-naphthyl-$C_1$ to $C_{12}$ alkyl group and a 2-naphthyl-$C_1$ to $C_{12}$ alkyl group. Among them, a $C_1$ to $C_{12}$ alkyloxyphenyl-$C_1$ to $C_{12}$ alkyl group and a $C_1$ to $C_{12}$ alkylphenyl-$C_1$ to $C_{12}$ alkyl group are preferred.

The arylalkyloxy group represented by $R^{P1}$, $R^{P2}$, $R^{P3}$, $R^{P4}$, $R^{P5}$ and $R^{P6}$ has usually 7 to 60 carbon atoms, and preferably 7 to 48 carbon atoms. The arylalkyloxy group may have a substituent. The number of carbon atoms described above does not include the number of carbon atoms of the substituent.

Examples of such arylalkyloxy group include a phenyl-$C_1$ to $C_{12}$ alkyloxy group such as a phenylmethyloxy group, a phenylethyloxy group, a phenylbutyloxy group, a phenylpentyloxy group, a phenylhexyloxy group, a phenylheptyloxy group and a phenyloctyloxy group; a $C_1$ to $C_{12}$ alkyloxyphenyl-$C_1$ to $C_{12}$ alkyloxy group; a $C_1$ to $C_{12}$ alkylphenyl-$C_1$ to $C_{12}$ alkyloxy group; a 1-naphthyl-$C_1$ to $C_{12}$ alkyloxy group; and a 2-naphthyl-$C_1$ to $C_{12}$ alkyloxy group. Among them, a $C_1$ to $C_{12}$ alkyloxyphenyl-$C_1$ to $C_{12}$ alkyloxy group and a $C_1$ to $C_{12}$ alkylphenyl-$C_1$ to $C_{12}$ alkyloxy group are preferred.

The arylalkylthio group represented by $R^{P1}$, $R^{P2}$, $R^{P3}$, $R^{P4}$, $R^{P5}$ and $R^{P6}$ has usually 7 to 60 carbon atoms, and preferably 7 to 48 carbon atoms. The arylalkylthio group may have a substituent. The number of carbon atoms described above does not include the number of carbon atoms of the substituent.

Examples of such arylalkylthio group include a phenyl-$C_1$ to $C_{12}$ alkylthio group, a $C_1$ to $C_{12}$ alkyloxyphenyl-$C_1$ to $C_{12}$ alkylthio group, a $C_1$ to $C_{12}$ alkylphenyl-$C_1$ to $C_{12}$ alkylthio group, a 1-naphthyl-$C_1$ to $C_{12}$ alkylthio group and a 2-naphthyl-$C_1$ to $C_{12}$ alkylthio group. Among them, a $C_1$ to $C_{12}$ alkyloxyphenyl-$C_1$ to $C_{12}$ alkylthio group and a $C_1$ to $C_{12}$ alkylphenyl-$C_1$ to $C_{12}$ alkylthio group are preferred.

The acyl group represented by $R^{P1}$, $R^{P2}$, $R^{P3}$, $R^{P4}$, $R^{P5}$ and $R^{P6}$ has usually 2 to 20 carbon atoms, and preferably 2 to 18 carbon atoms. The acyl group may have a substituent. The number of carbon atoms described above does not include the number of carbon atoms of the substituent.

Examples of such acyl group include an acetyl group, a propionyl group, a butyryl group, an isobutyryl group, a pivaloyl group, a benzoyl group, a trifluoroacetyl group and a pentafluorobenzoyl group.

The acyloxy group represented by $R^{P1}$, $R^{P2}$, $R^{P3}$, $R^{P4}$, $R^{P5}$ and $R^{P6}$ has usually 2 to 20 carbon atoms, and preferably 2 to 18 carbon atoms. The acyloxy group may have a substituent. The number of carbon atoms described above does not include the number of carbon atoms of the substituent.

Examples of such acyloxy group include an acetoxy group, a propionyloxy group, a butyryloxy group, an isobutyryloxy group, a pivaloyloxy group, a benzoyloxy group, a trifluoroacetyloxy group and a pentafluorobenzoyloxy group.

The carbamoyl group represented by $R^{P1}$, $R^{P2}$, $R^{P3}$, $R^{P4}$, $R^{P5}$ and $R^{P6}$ may have a substituent and has, including the number of carbon atoms of the substituent, usually 1 to 20 carbon atoms, and preferably 2 to 18 carbon atoms (that is, the carbamoyl group is represented by a general formula: $NR^aR^b$—CO— wherein $R^a$ and $R^b$ each independently represent a hydrogen atom or a substituent).

Examples of such carbamoyl group include an aminocarbonyl group, a methylaminocarbonyl group, a dimethylaminocarbonyl group, an ethylaminocarbonyl group, a propylaminocarbonyl group and a butylaminocarbonyl group.

The amido group represented by $R^{P1}$, $R^{P2}$, $R^{P3}$, $R^{P4}$, $R^{P5}$ and $R^{P6}$ may have a substituent and has, including the number of carbon atoms of the substituent, usually 1 to 20 carbon atoms, and preferably 2 to 18 carbon atoms (that is, the amido group is represented by a general formula: $R^c$—CO—$NR^d$— wherein $R^c$ and $R^d$ each independently represent a hydrogen atom or a substituent).

Examples of such amido group include a formamido group, an acetamido group, a propioamido group, a butyramido group, a benzamido group, a trifluoroacetamido group, a pentafluorobenzamido group, a diformamido group, a diacetamido group, a dipropioamido group, a dibutyramido group, a dibenzamido group, a ditrifluoroacetamido group and a dipentafluorobenzamido group.

The acid imido group represented by $R^{P1}$, $R^{P2}$, $R^{P3}$, $R^{P4}$, $R^{P5}$ and $R^{P6}$ means a monovalent residue that is obtained by removing, from an acid imide, one hydrogen atom bonded to a nitrogen atom thereof. The acid imido group has usually 2 to 60 carbon atoms, and preferably 2 to 48 carbon atoms. The acid imido group may have a substituent. The number of carbon atoms described above does not include the number of carbon atoms of the substituent.

Examples of such acid imido group include groups indicated by structural formulae below.

[Chem. 7]

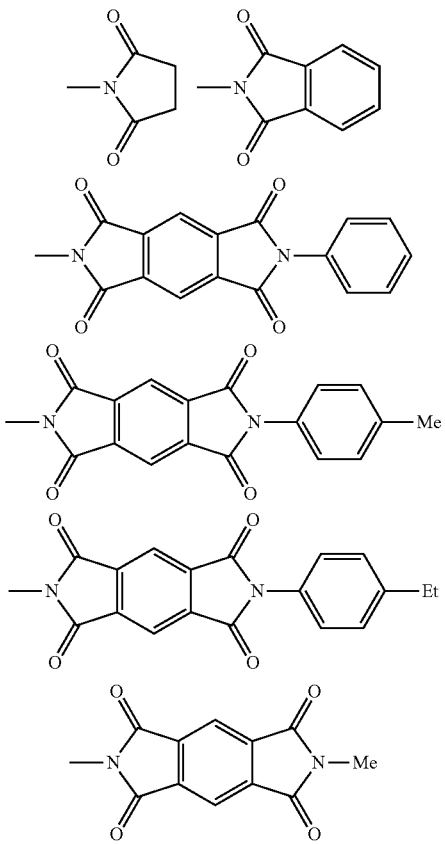

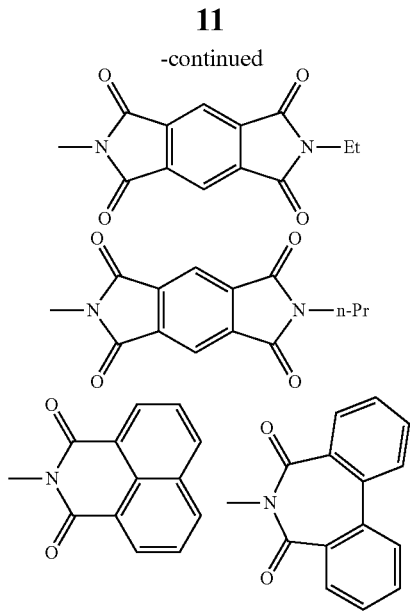

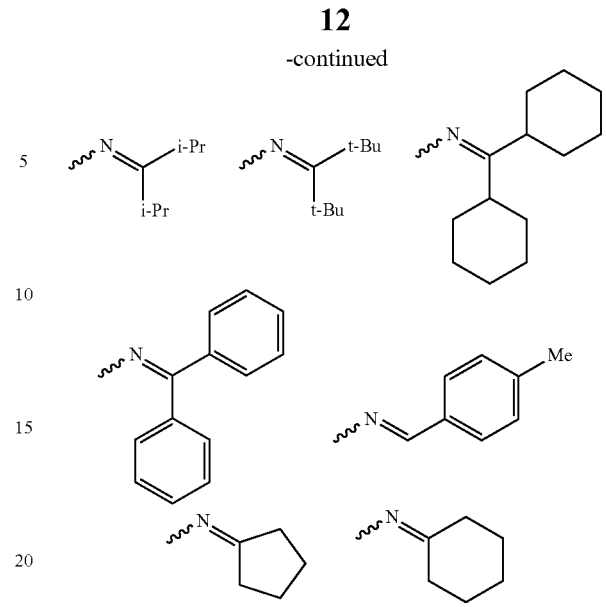

In the formulae, a line extending from a nitrogen atom represents a bond, Me represents a methyl group, Et represents an ethyl group, and n-Pr represents an n-propyl group. The same shall apply hereinafter.

The imine residue represented by $R^{P1}$, $R^{P2}$, $R^{P3}$, $R^{P4}$, $R^{P5}$ and $R^{P6}$ means a monovalent residue remaining after removing one hydrogen atom from an imine compound (that is, an organic compound having —N═C— in the molecule thereof. Examples thereof include aldimine, ketimine, and a compound in which a hydrogen atom bonded to a nitrogen atom in the molecule thereof is substituted with an alkyl group or the like). The imine residue has usually 2 to 20 carbon atoms, and preferably 2 to 18 carbon atoms. The imine residue may have a substituent. The number of carbon atoms described above does not include the number of carbon atoms of the substituent.

Examples of such imine residue include groups indicated by structural formulae below.

[Chem. 8]

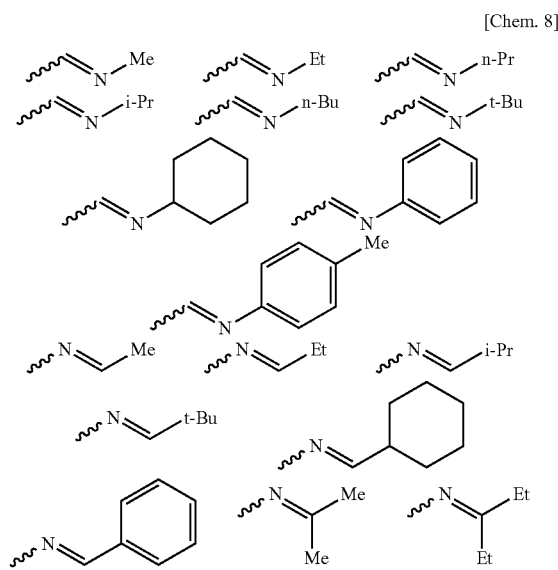

In the formulae, i-Pr represents an isopropyl group, n-Bu represents an n-butyl group, and t-Bu represents a tert-butyl group. A bond indicated by a wavy line means that the bond is a "bond represented by a wedge-shape" and/or a "bond represented by a broken line". Here, the "bond represented by a wedge-shape" means a bond projecting from the surface of the paper toward the front, and the "bond represented by a broken line" means a bond projecting from the surface of the paper toward the back.

The substituted amino group represented by $R^{P1}$, $R^{P2}$, $R^{P3}$, $R^{P4}$, $R^{P5}$ and $R^{P6}$ means an amino group in which one or two hydrogen atoms of an amino group are substituted with one or two groups selected from the group consisting of an alkyl group, an aryl group, an arylalkyl group and a monovalent heterocyclic group. Although the alkyl group, the aryl group, the arylalkyl group and the monovalent heterocyclic group may have a substituent, the number of carbon atoms of the substituent is not included in the number of carbon atoms of the substituted amino group. The substituted amino group has usually 1 to 60 carbon atoms, and preferably 2 to 48 carbon atoms.

Examples of such substituted amino group include a methylamino group, a dimethylamino group, an ethylamino group, a diethylamino group, a propylamino group, a dipropylamino group, an iso-propylamino group, a diisopropylamino group, a butylamino group, an iso-butylamino group, a tert-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamino group, a laurylamino group, a cyclopentylamino group, a dicyclopentylamino group, a cyclohexylamino group, a dicyclohexylamino group, a pyrrolidyl group, a piperidyl group, a ditrifluoromethylamino group, a phenylamino group, a diphenylamino group, a $C_1$ to $C_{12}$ alkyloxyphenylamino group, a di ($C_1$ to $C_{12}$ alkyloxyphenyl) amino group, a di ($C_1$ to $C_{12}$ alkylphenyl)amino group, a 1-naphthylamino group, a 2-naphthylamino group, a pentafluorophenylamino group, a pyridylamino group, a pyridazinylamino group, a pyrimidylamino group, a pyridylamino group, a triazylamino group, a phenyl-$C_1$ to $C_{12}$ alkylamino group, a $C_1$ to $C_{12}$ alkyloxyphenyl-$C_1$ to $C_{12}$ alkylamino group, a $C_1$ to $C_{12}$ alkylphenyl-$C_1$ to $C_{12}$ alkylamino group, a di($C_1$ to $C_{12}$ alkyloxyphenyl-$C_1$ to $C_{12}$ alkyl)amino group, a di ($C_1$ to $C_{12}$ alkylphenyl-$C_1$ to $C_{12}$ alkyl)amino group, a 1-naphthyl-$C_1$ to $C_{12}$ alkylamino group and a 2-naphthyl-$C_1$ to $C_{12}$ alkylamino group.

The substituted silyl group represented by $R^{P1}$, $R^{P2}$, $R^{P3}$, $R^{P4}$, $R^{P5}$ and $R^{P6}$ means a silyl group in which one, two or three hydrogen atoms of a silyl group are substituted with one, two or three groups selected from the group consisting of an alkyl group, an aryl group, an arylalkyl group and a monovalent heterocyclic group. Although the alkyl group, the aryl group, the arylalkyl group and the monovalent heterocyclic group may have a substituent, the number of carbon atoms of the substituent is not included in the number of carbon atoms of the substituted silyl group. The substituted silyl group has usually 1 to 60 carbon atoms, and preferably 3 to 48 carbon atoms.

Examples of such substituted silyl group include a trimethylsilyl group, a triethylsilyl group, a tripropylsilyl group, a tri-iso-propylsilyl group, a dimethyl-iso-propylsilyl group, a diethyl-iso-propylsilyl group, a tert-butylsilyldimethylsilyl group, a pentyldimethylsilyl group, a hexyldimethylsilyl group, a heptyldimethylsilyl group, an octyldimethylsilyl group, a 2-ethylhexyl-dimethylsilyl group, a nonyldimethylsilyl group, a decyldimethylsilyl group, a 3,7-dimethyloctyl-dimethylsilyl group, a lauryldimethylsilyl group, a phenyl-$C_1$ to $C_{12}$ alkylsilyl group, a $C_1$ to $C_{12}$ alkyloxyphenyl-$C_1$ to $C_{12}$ alkylsilyl group, a $C_1$ to $C_{12}$ alkylphenyl-$C_1$ to $C_{12}$ alkylsilyl group, a 1-naphthyl-$C_1$ to $C_{12}$ alkylsilyl group, a 2-naphthyl-$C_1$ to $C_{12}$ alkylsilyl group, a phenyl-$C_1$ to $C_{12}$ alkyldimethylsilyl group, a triphenylsilyl group, a tri-p-xylylsilyl group, a tribenzylsilyl group, a diphenylmethylsilyl group, a tert-butyldiphenylsilyl group and a dimethylphenylsilyl group.

The substituted silyloxy group represented by $R^{P1}$, $R^{P2}$, $R^{P3}$, $R^{P4}$, $R^{P5}$ and $R^{P6}$ means a silyloxy group in which one, two or three hydrogen atoms of a silyloxy group are substituted with one, two or three groups selected from the group consisting of an alkyl group, an aryl group, an arylalkyl group and a monovalent heterocyclic group. Although the alkyl group, the aryl group, the arylalkyl group and the monovalent heterocyclic group may have a substituent, the number of carbon atoms of the substituent is not included in the number of carbon atoms of the substituted silyloxy group. The substituted silyloxy group has usually 1 to 60 carbon atoms, and preferably 3 to 48 carbon atoms.

Examples of such substituted silyloxy group include a trimethylsilyloxy group, a triethylsilyloxy group, a tripropylsilyloxy group, a tri-iso-propylsilyloxy group, a dimethyl-iso-propylsilyloxy group, a diethyl-iso-propylsilyloxy group, a tert-butylsilyldimethylsilyloxy group, a pentyldimethylsilyloxy group, a hexyldimethylsilyloxy group, a heptyldimethylsilyloxy group, an octyldimethylsilyloxy group, a 2-ethylhexyl-dimethylsilyloxy group, a nonyldimethylsilyloxy group, a decyldimethylsilyloxy group, a 3,7-dimethyloctyl-dimethylsilyloxy group, a lauryldimethylsilyloxy group, a phenyl-$C_1$ to $C_{12}$ alkylsilyloxy group, a $C_1$ to $C_{12}$ alkyloxyphenyl-$C_1$ to $C_{12}$ alkylsilyloxy group, a $C_1$ to $C_{12}$ alkylphenyl-$C_1$ to $C_{12}$ alkylsilyloxy group, a 1-naphthyl-$C_1$ to $C_{12}$ alkylsilyloxy group, a 2-naphthyl-$C_1$ to $C_{12}$ alkylsilyloxy group, a phenyl-$C_1$ to $C_{12}$ alkyldimethylsilyloxy group, a triphenylsilyloxy group, a tri-p-xylylsilyloxy group, a tribenzylsilyloxy group, a diphenylmethylsilyloxy group, a tert-butyldiphenylsilyloxy group and a dimethylphenylsilyloxy group.

The substituted silylthio group represented by $R^{P1}$, $R^{P2}$, $R^{P3}$, $R^{P4}$, $R^{P5}$ and $R^{P6}$ means a silylthio group in which one, two or three hydrogen atoms of a silylthio group are substituted with one, two or three groups selected from the group consisting of an alkyl group, an aryl group, an arylalkyl group and a monovalent heterocyclic group. Although the alkyl group, the aryl group, the arylalkyl group and the monovalent heterocyclic group may have a substituent, the number of carbon atoms of the substituent is not included in the number of carbon atoms of the substituted silylthio group. The substituted silylthio group has usually 1 to 60 carbon atoms, and preferably 3 to 48 carbon atoms.

Examples of such substituted silylthio group include a trimethylsilylthio group, a triethylsilylthio group, a tripropylsilylthio group, a tri-iso-propylsilylthio group, a dimethyl-iso-propylsilylthio group, a diethyl-iso-propylsilylthio group, a tert-butylsilyldimethylsilylthio group, a pentyldimethylsilylthio group, a hexyldimethylsilylthio group, a heptyldimethylsilylthio group, an octyldimethylsilylthio group, a 2-ethylhexyl-dimethylsilylthio group, a nonyldimethylsilylthio group, a decyldimethylsilylthio group, a 3,7-dimethyloctyl-dimethylsilylthio group, a lauryldimethylsilylthio group, a phenyl-$C_1$ to $C_{12}$ alkylsilylthio group, a $C_1$ to $C_{12}$ alkyloxyphenyl-$C_1$ to $C_{12}$ alkylsilylthio group, a $C_1$ to $C_{12}$ alkylphenyl-$C_1$ to $C_{12}$ alkylsilylthio group, a 1-naphthyl-$C_1$ to $C_{12}$ alkylsilylthio group, a 2-naphthyl-$C_1$ to $C_{12}$ alkylsilylthio group, a phenyl-$C_1$ to $C_{12}$ alkyldimethylsilylthio group, a triphenylsilylthio group, a tri-p-xylylsilylthio group, a tribenzylsilylthio group, a diphenylmethylsilylthio group, a tert-butyldiphenylsilylthio group and a dimethylphenylsilylthio group.

The substituted silylamino group represented by $R^{P1}$, $R^{P2}$, $R^{P3}$, $R^{P4}$, $R^{P5}$ and $R^{P6}$ means a silylamino group in which one, two or three hydrogen atoms of a silylamino group are substituted with one, two or three groups selected from the group consisting of an alkyl group, an aryl group, an arylalkyl group and a monovalent heterocyclic group. Although the alkyl group, the aryl group, the arylalkyl group and the monovalent heterocyclic group may have a substituent, the number of carbon atoms of the substituent is not included in the number of carbon atoms of the substituted silylamino group. The substituted silylamino group has usually 1 to 60 carbon atoms, and preferably 3 to 48 carbon atoms.

Examples of such substituted silylamino group include a trimethylsilylamino group, a triethylsilylamino group, a tripropylsilylamino group, a tri-iso-propylsilylamino group, a dimethyl-iso-propylsilylamino group, a diethyl-iso-propylsilylamino group, a tert-butylsilyldimethylsilylamino group, a pentyldimethylsilylamino group, a hexyldimethylsilylamino group, a heptyldimethylsilylamino group, an octyldimethylsilylamino group, a 2-ethylhexyl-dimethylsilylamino group, a nonyldimethylsilylamino group, a decyldimethylsilylamino group, a 3,7-dimethyloctyl-dimethylsilylamino group, a lauryldimethylsilylamino group, a phenyl-$C_1$ to $C_{12}$ alkylsilylamino group, a $C_1$ to $C_{12}$ alkyloxyphenyl-$C_1$ to $C_{12}$ alkylsilylamino group, a $C_1$ to $C_{12}$ alkylphenyl-$C_1$ to $C_{12}$ alkylsilylamino group, a 1-naphthyl-$C_1$ to $C_{12}$ alkylsilylamino group, a 2-naphthyl-$C_1$ to $C_{12}$ alkylsilylamino group, a phenyl-$C_1$ to $C_{12}$ alkyldimethylsilylamino group, a triphenylsilylamino group, a tri-p-xylylsilylamino group, a tribenzylsilylamino group, a diphenylmethylsilylamino group, a tert-butyldiphenylsilylamino group and a dimethylphenylsilylamino group.

The monovalent heterocyclic group represented by $R^{P1}$, $R^{P2}$, $R^{P3}$, $R^{P4}$, $R^{P5}$ and $R^{P6}$ means an atomic group remaining after removing one hydrogen atom from a heterocyclic compound. The monovalent heterocyclic group has usually 4 to 60 carbon atoms, and preferably 4 to 20 carbon atoms. The monovalent heterocyclic group may have a substituent. The number of carbon atoms described above does not include the number of carbon atoms of the substituent. Here, the heterocyclic compound refers to a compound containing not only a carbon atom but also a hetero atom such as an oxygen atom, a sulfur atom, a nitrogen atom, a phosphorus atom and a boron atom as an element constituting the ring, among organic compounds having a cyclic structure.

Examples of such monovalent heterocyclic group include a thienyl group, a $C_1$ to $C_{12}$ alkylthienyl group, a pyrrolyl group, a furyl group, a pyridyl group, a $C_1$ to $C_{12}$ alkylpyridyl group, a piperidyl group, a quinolyl group, and an isoquinolyl group. Among them, a thienyl group, a $C_1$ to $C_{12}$ alkylthienyl group, a pyridyl group and a $C_1$ to $C_{12}$ alkylpyridyl group are preferred.

The heteroaryloxy group represented by $R^{P1}$, $R^{P2}$, $R^{P3}$, $R^{P4}$, $R^{P5}$ and $R^{P6}$ has usually 6 to 60 carbon atoms, and preferably 7 to 48 carbon atoms. The heteroaryloxy group may have a substituent. The number of carbon atoms described above does not include the number of carbon atoms of the substituent.

Examples of such heteroaryloxy group include a thienyloxy group, a $C_1$ to $C_{12}$ alkyloxythienyloxy group, a $C_1$ to $C_{12}$ alkylthienyloxy group, a pyridyloxy group, a $C_1$ to $C_{12}$ alkyloxypyridyloxy group, a $C_1$ to $C_{12}$ alkylpyridyloxy group and an isoquinolyloxy group. Among them, a $C_1$ to $C_{12}$ alkyloxypyridyloxy group and a $C_1$ to $C_{12}$ alkylpyridyloxy group are preferred.

Examples of the $C_1$ to $C_{12}$ alkylpyridyloxy group include a methylpyridyloxy group, an ethylpyridyloxy group, a dimethylpyridyloxy group, a propylpyridyloxy group, a 1,3,5-trimethylpyridyloxy group, a methylethylpyridyloxy group, an iso-propylpyridyloxy group, a butylpyridyloxy group, an iso-butylpyridyloxy group, a tert-butylpyridyloxy group, a pentylpyridyloxy group, an isoamylpyridyloxy group, a hexylpyridyloxy group, a heptylpyridyloxy group, an octylpyridyloxy group, a nonylpyridyloxy group, a decylpyridyloxy group and a dodecylpyridyloxy group.

The heteroarylthio group represented by $R^{P1}$, $R^{P2}$, $R^{P3}$, $R^{P4}$, $R^{P5}$ and $R^{P6}$ has usually 6 to 60 carbon atoms, and preferably 7 to 48 carbon atoms. The heteroarylthio group may have a substituent. The number of carbon atoms described above does not include the number of carbon atoms of the substituent.

Examples of such heteroarylthio group include a pyridylthio group, a $C_1$ to $C_{12}$ alkyloxypyridylthio group, a $C_1$ to $C_{12}$ alkylpyridylthio group and an isoquinolylthio group. Among them, a $C_1$ to $C_{12}$ alkyloxypyridylthio group and a $C_1$ to $C_{12}$ alkylpyridylthio group are preferred.

The arylalkenyl group represented by $R^{P1}$, $R^{P2}$, $R^{P3}$, $R^{P4}$, $R^{P5}$ and $R^{P6}$ has usually 7 to 60 carbon atoms, and preferably 7 to 48 carbon atoms. The arylalkenyl group may have a substituent. The number of carbon atoms described above does not include the number of carbon atoms of the substituent.

Examples of such arylalkenyl group include a phenyl-$C_2$ to $C_{12}$ alkenyl group ("$C_2$ to $C_{12}$ alkenyl" means that the alkenyl moiety has 2 to 12 carbon atoms, and the same shall apply hereinafter), a $C_1$ to $C_{12}$ alkyloxyphenyl-$C_2$ to $C_{12}$ alkenyl group, a $C_1$ to $C_{12}$ alkylphenyl-$C_2$ to $C_{12}$ alkenyl group, a 1-naphthyl-$C_2$ to $C_{12}$ alkenyl group and a 2-naphthyl-$C_2$ to $C_{12}$ alkenyl group. Among them, a $C_1$ to $C_{12}$ alkyloxyphenyl-$C_2$ to $C_{12}$ alkenyl group and a $C_2$ to $C_{12}$ alkylphenyl-$C_1$ to $C_{12}$ alkenyl group are preferred.

Examples of the $C_2$ to $C_{12}$ alkenyl include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

The arylalkynyl group represented by $R^{P1}$, $R^{P2}$, $R^{P3}$, $R^{P4}$, $R^{P5}$ and $R^{P6}$ has usually 7 to 60 carbon atoms, and preferably 7 to 48 carbon atoms. The arylalkynyl group may have a substituent. The number of carbon atoms described above does not include the number of carbon atoms of the substituent.

Examples of such arylalkynyl group include a phenyl-$C_2$ to $C_{12}$ alkynyl group ("$C_2$ to $C_{12}$ alkynyl" means that the alkynyl moiety has 2 to 12 carbon atoms, and the same shall apply hereinafter), a $C_1$ to $C_{12}$ alkyloxyphenyl-$C_2$ to $C_{12}$ alkynyl group, a $C_1$ to $C_{12}$ alkylphenyl-$C_2$ to $C_{12}$ alkynyl group, a 1-naphthyl-$C_2$ to $C_{12}$ alkynyl group, and a 2-naphthyl-$C_2$ to $C_{12}$ alkynyl group. Among them, a $C_1$ to $C_{12}$ alkyloxyphenyl-$C_2$ to $C_{12}$ alkynyl group and a $C_1$ to $C_{12}$ alkylphenyl-$C_2$ to $C_{12}$ alkynyl group are preferred.

Examples of the above $C_2$ to $C_{12}$ alkynyl may include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl and 1-octynyl.

The substituted carboxyl group represented by $R^{P1}$, $R^{P2}$, $R^{P3}$, $R^{P4}$, $R^{P5}$ and $R^{P6}$ (the substituted carboxyl group is represented by a general formula: $R^e$—O—CO— wherein $R^e$ represents an alkyl group, an aryl group, an arylalkyl group or a monovalent heterocyclic group) has usually 1 to 60 carbon atoms, and preferably 2 to 48 carbon atoms. The substituted carboxyl group means a carboxyl group in which a hydrogen atom is substituted with an alkyl group, an aryl group, an arylalkyl group or a monovalent heterocyclic group. Although the alkyl group, the aryl group, the arylalkyl group or the monovalent heterocyclic group may have a substituent, the number of carbon atoms of the substituent is not included in the number of carbon atoms described above.

Examples of such a substituted carboxyl group may include a methyloxycarbonyl group, an ethyloxycarbonyl group, a propyloxycarbonyl group, an iso-propyloxycarbonyl group, a butyloxycarbonyl group, an iso-butyloxycarbonyl group, a tert-butyloxycarbonyl group, a pentyloxycarbonyl group, a hexyloxycarbonyl group, a cyclohexyloxycarbonyl group, a heptyloxycarbonyl group, an octyloxycarbonyl group, a 2-ethylhexyloxycarbonyl group, a nonyloxycarbonyl group, a decyloxycarbonyl group, a 3,7-dimethyloctyloxycarbonyl group, a dodecyloxycarbonyl group, a trifluoromethyloxycarbonyl group, a pentafluoroethyloxycarbonyl group, a perfluorobutyloxycarbonyl group, a perfluorohexyloxycarbonyl group, a perfluorooctyloxycarbonyl group, a pyridyloxycarbonyl group, a naphthyloxycarbonyl group and a pyridyloxycarbonyl group.

When the groups noted above have a substituent, examples of the substituent include a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group and a cyano group. The details of these groups are the same as those described and exemplified above. The substituent is preferably a halogen atom, an alkyl group, an alkyloxy group, an aryl group or a monovalent heterocyclic group, and more preferably an alkyl group, an aryl group or a monovalent heterocyclic group. When the groups noted above have a substituent, the number of substituents is usually 1 to 3, preferably 1 to 2, and more preferably 1.

In the metal complex of the present invention, at least one of $R^{P1}$ to $R^{P4}$ is preferably a substituent having electron-acceptor characteristics, and more preferably a fluorine atom or a substituent containing a fluorine atom. In the present invention, the fluorine atom or the substituent containing a fluorine atom represents a monovalent group indicated by $C_pF_qH_rC_s$. Here, p represents an integer selected from 1 to 10, q represents an integer selected from 1 to (2p+1), r represents an integer selected from 0 to (2p+1), and s is 0 or 1. Examples thereof include groups indicated by Formulae (F1) to (F14) and Formulae (F24) to (F32).

[Chem. 9]

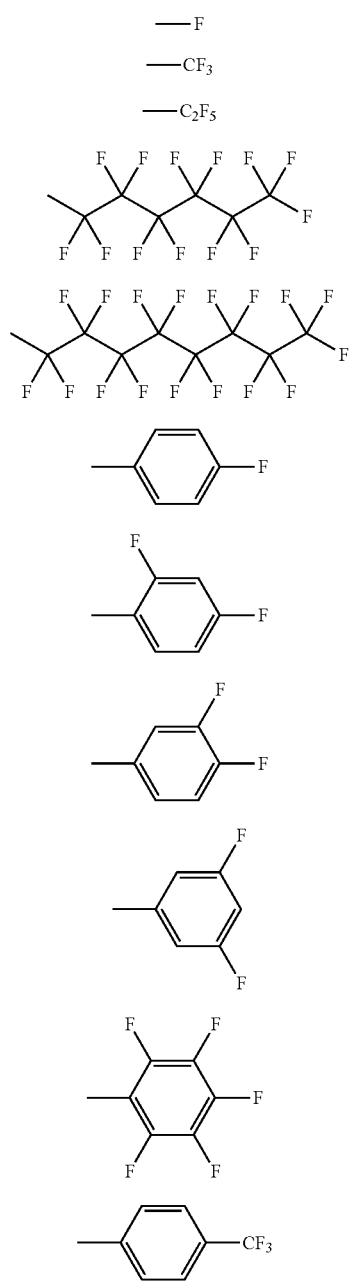

[Chem. 10]

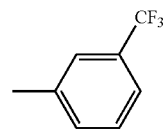
(F12)

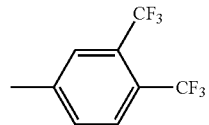
(F13)

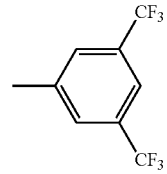
(F14)

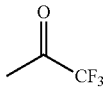
(F24)

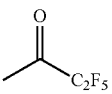
(F25)

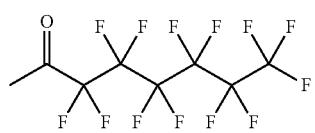
(F26)

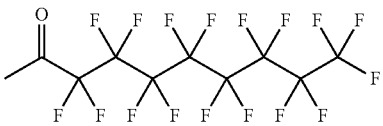
(F27)

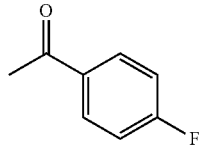
(F28)

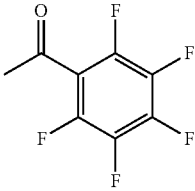
(F29)

(F30)

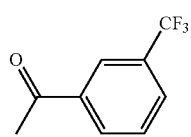
(F31)

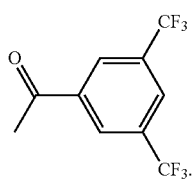 (F32)

From the viewpoint of the chemical stability of the metal complex of the present invention, it is preferable that, in the monovalent group indicated by $C_pF_qH_rO_s$ is 0. Accordingly, the monovalent group is preferably a group indicated by Formulae (F1) to (F14).

Although the bidentate ligand, which is a portion represented by Formula (2), is not limited, the bidentate ligand is preferably monoanionic so that the metal complex of the present invention is neutral. Examples thereof include structures below.

[Chem. 11]

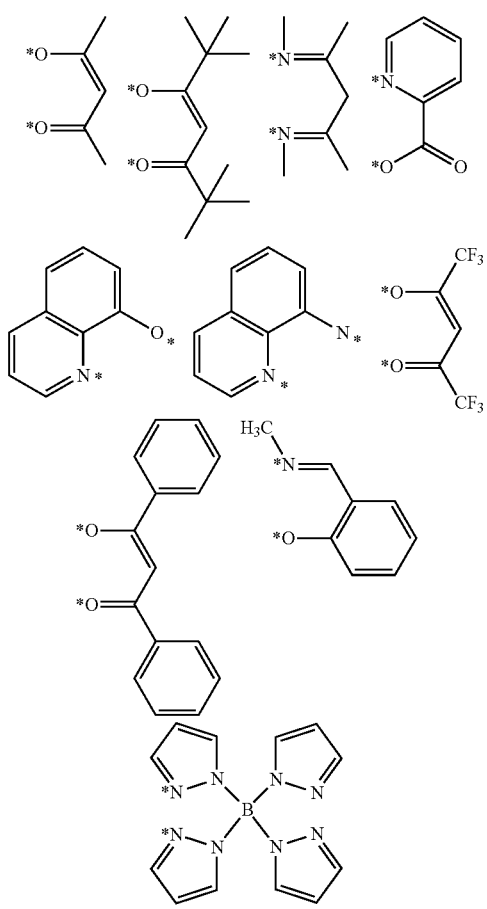

[Chem. 12]

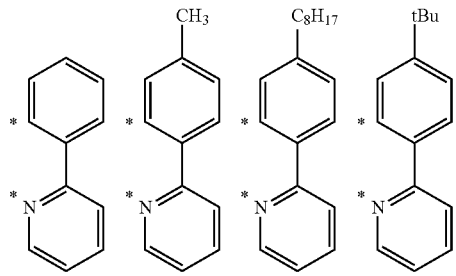

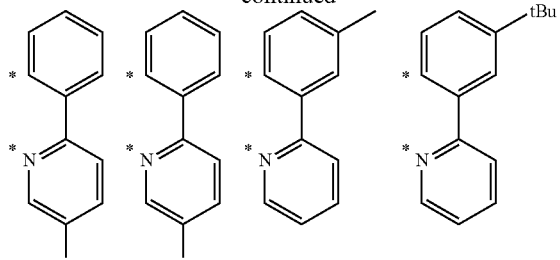

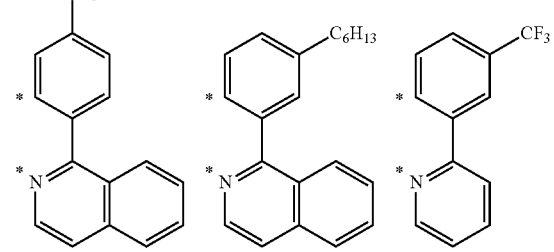

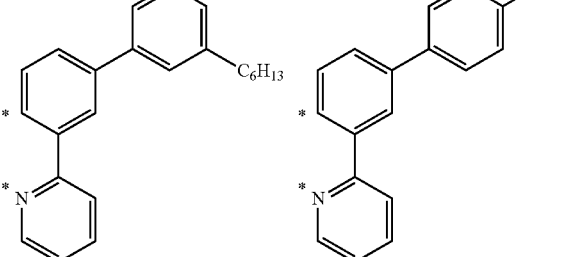

In the formulae, * represents a position bonding to the metal atom M.

Examples of the metal complex of the present invention include structures represented by formulae below.

[Chem. 13]

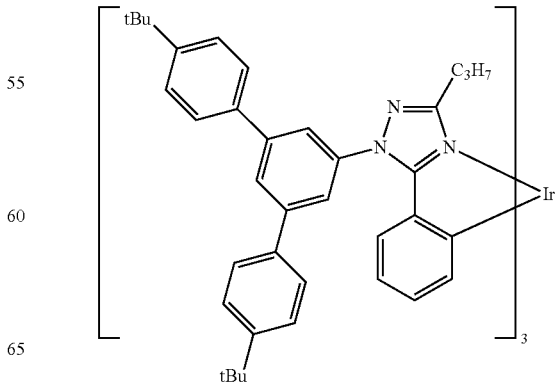

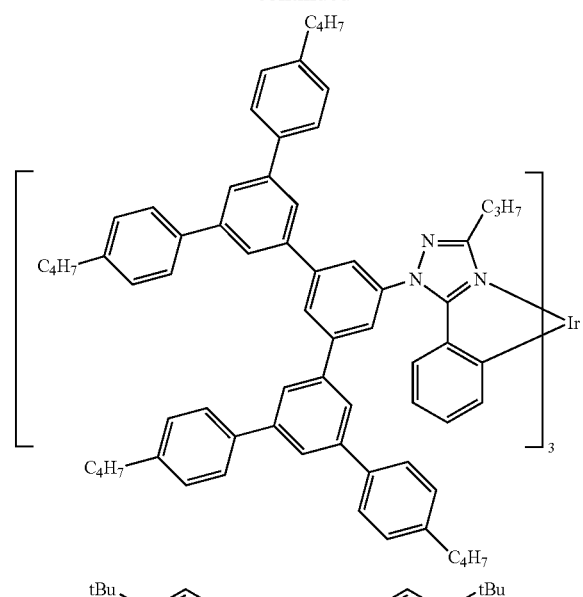
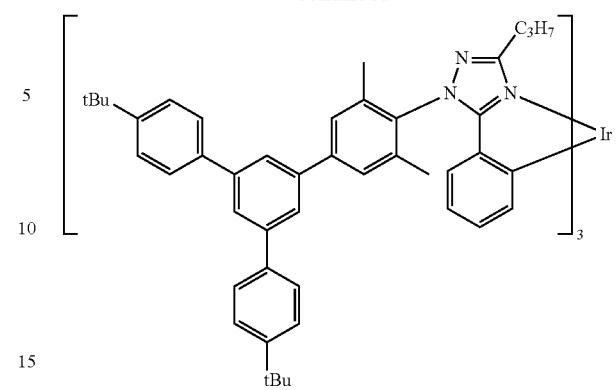
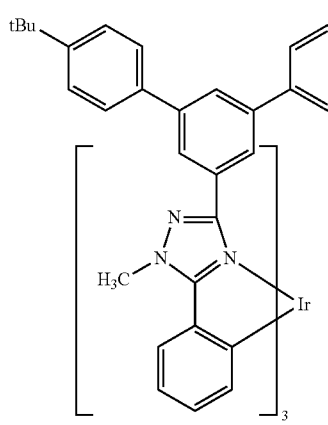
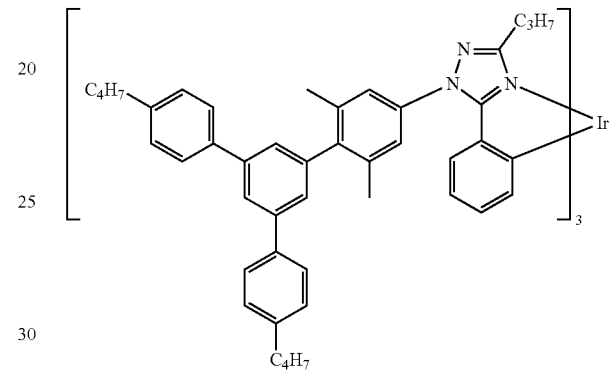
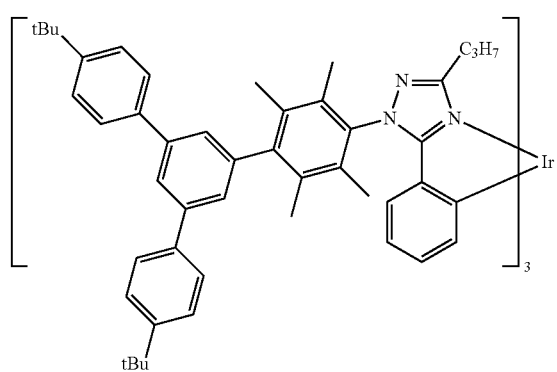
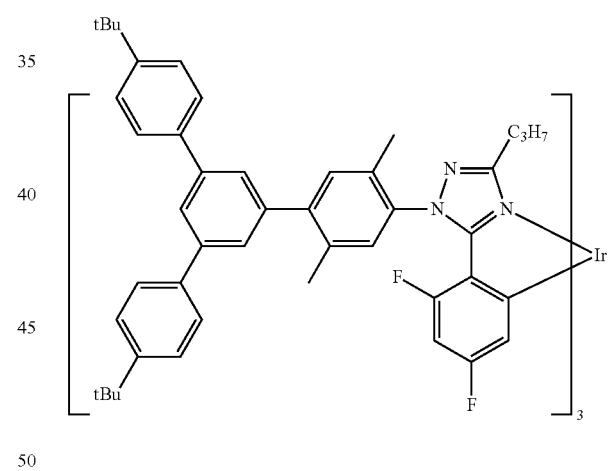
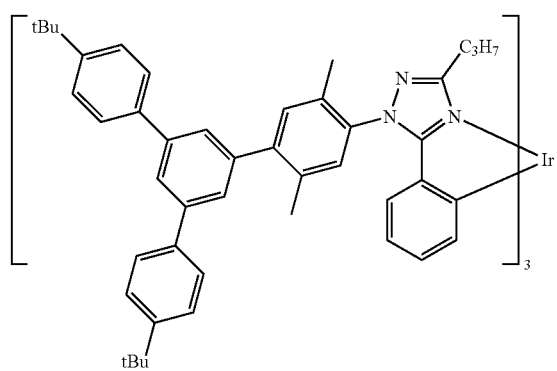
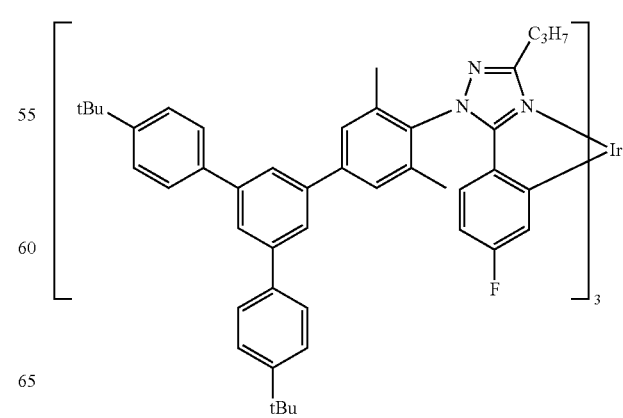

23
-continued
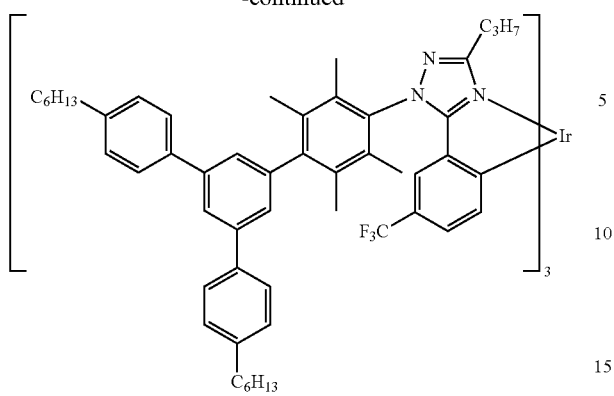
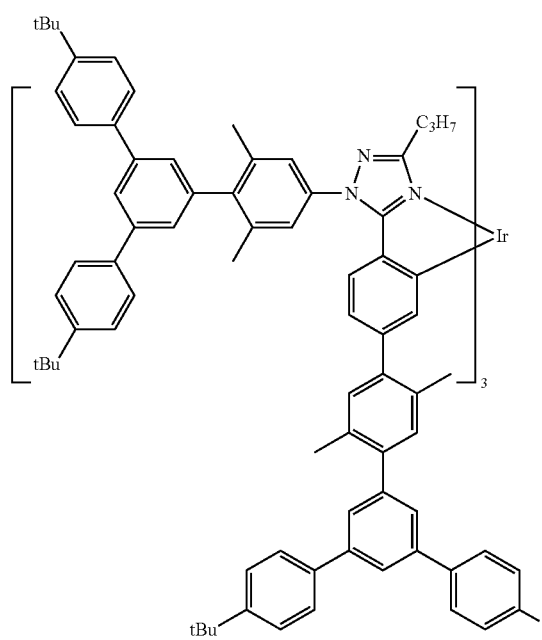
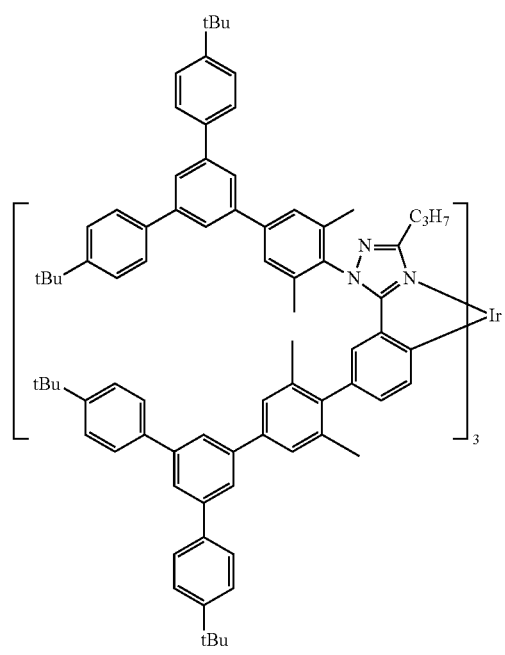
24
-continued
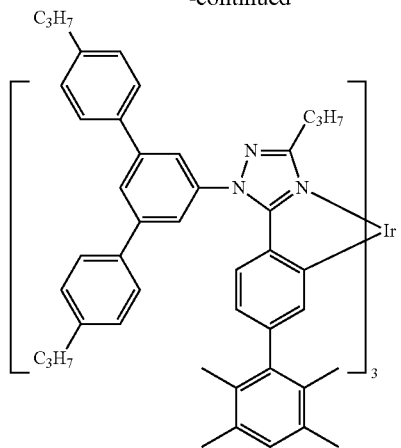
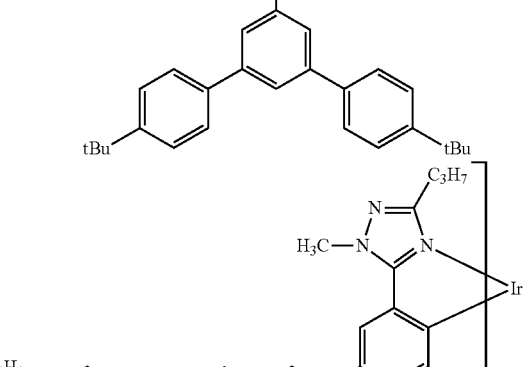
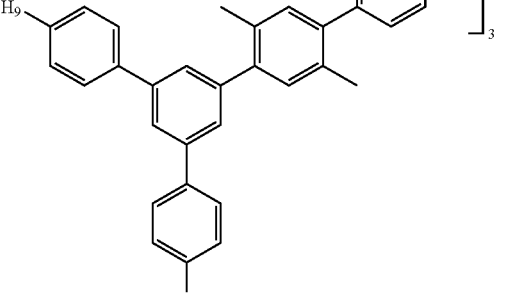
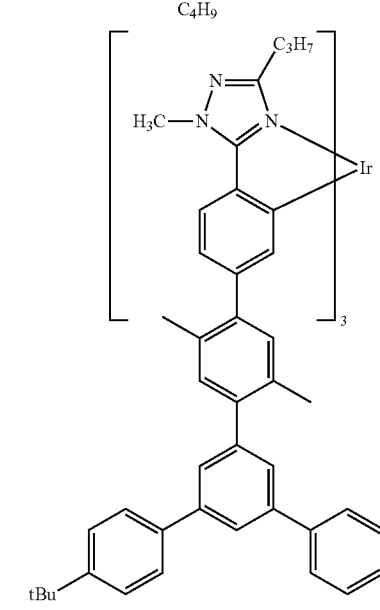

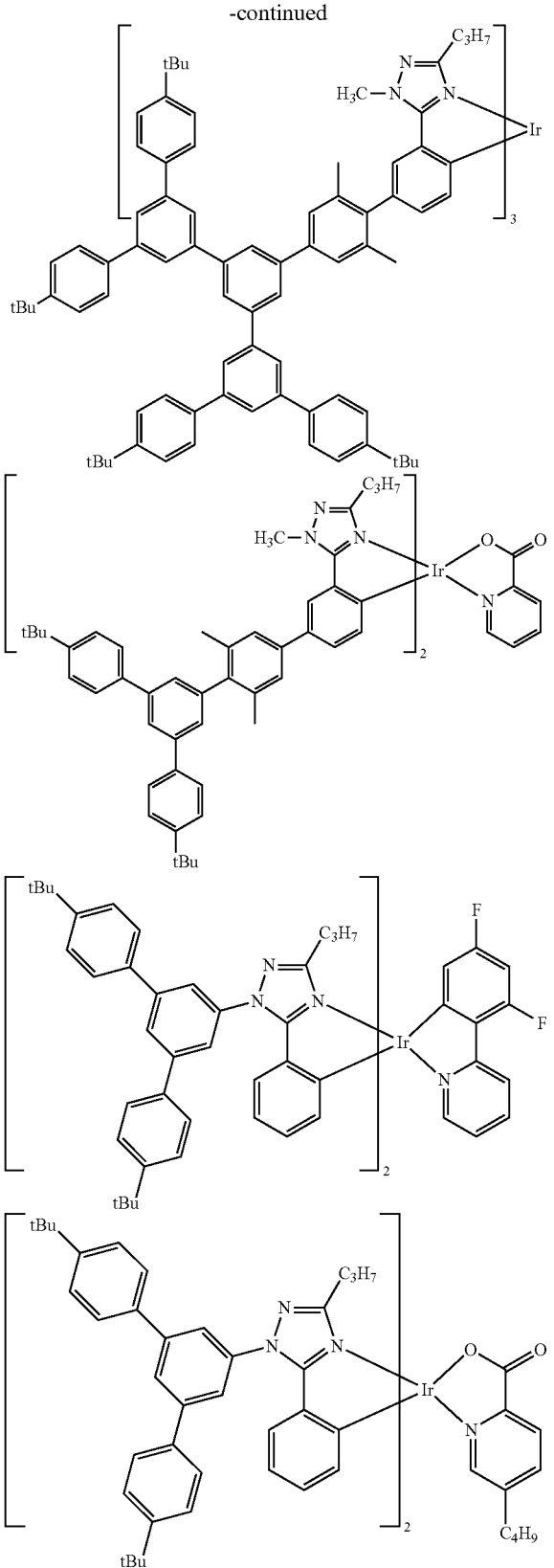

—Method for Manufacturing Metal Complex—

Next, a method for synthesizing the metal complex of the present invention will be described.

The metal complex of the present invention can be synthesized, for example, by reacting a compound to be a ligand with a metal compound in a solvent. If necessary, a base, a silver chloride compound or the like may exist in the reaction system. The metal complex of the present invention can be synthesized by a coupling reaction of a metal complex having a 5-phenyl-1,2,4-triazole derivative as a ligand and an aromatic heterocyclic compound.

The method of complexation (that is, the method for reacting a compound to be a ligand with a metal compound in a solution) include:

in the case of a complex having an iridium atom, methods described in J. Am. Chem. Soc. 1984, 106, 6647; Inorg. Chem. 1991, 30, 1685; Inorg. Chem. 1994, 33, 545; Inorg. Chem. 2001, 40, 1704; Chem. Lett., 2003, 32, 252; and the like, in the case of a complex having a platinum atom, methods described in Inorg. Chem., 1984, 23, 4249; Chem. Mater. 1999, 11, 3709; Organometallics, 1999, 18, 1801; and the like, and in the case of a complex having a palladium atom, methods described in J. Org. Chem., 1987, 52, 73, and the like.

Although a reaction temperature for the complexation is not limited, it is usually between the melting point and the boiling point of a solvent, and preferably from −78° C. to the boiling point of a solvent. Although a reaction time is not limited, it is usually from 30 minutes to 30 hours. When a microwave reaction apparatus is used for the complexation reaction, the reaction can be carried out at the boiling point of a solvent or higher, and although the reaction time is not limited, it is from several minutes to several hours.

The compound to be a ligand can be synthesized, for example, by Suzuki coupling, Grignard coupling, Stille coupling or the like of a 5-phenyl-1,2,4-triazole and an aromatic heterocyclic compound. If necessary, the compound can be synthesized by dissolving reactants in an organic solvent and, for example, reacting them at a temperature of the melting point or higher and the boiling point or lower of the organic solvent, using a base, an appropriate catalyst, etc. For such synthesis, there can be used methods described in, for example: "Organic Syntheses", Collective Volume VI, pp. 407-411, John Wiley & Sons, Inc., 1988; Chem. Rev., vol. 106, p. 2651 (2006); Chem. Rev., vol. 102, p. 1359 (2002); Chem. Rev., vol. 95, p. 2457 (1995); J. Organomet. Chem., vol. 576, p. 147 (1999); and the like.

The aromatic heterocyclic compound can be synthesized by methods described in "HOUBEN-WEYL METHODS OF ORGANIC CHEMISTRY 4$^{TH}$ EDITION", vol. E9b, p. 1 (GEORG THIEME VERLAG STUTTGART); HOUBEN-WEYL METHODS OF ORGANIC CHEMISTRY 4$^{TH}$ EDITION, vol. E9c, p. 667 (GEORG THIEME VERLAG STUTTGART); and the like.

An identification and an analysis of the obtained compound can be performed with CHN elementary analysis, NMR analysis, MS analysis and X-ray crystal structure analysis.

<Composition>

The composition of the present invention comprises the metal complex of the present invention and a charge transport compound (that is, charge transport material), and may further contain a light-emitting material.

The charge transport material is classified into a hole transport material and an electron transport material. Specifically, an organic compound (a low molecular compound and/or a polymer compound) can be used for the charge transport material. The charge transport material is preferably a polymer compound.

The hole transport material includes compounds publicly known as hole transport materials for organic electroluminescent device, such as aromatic amines, carbazole derivatives and polyparaphenylene derivatives. The electron transport material includes compounds publicly known as electron transport materials for organic electroluminescent device, for example, oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, and metal complexes of 8-hydroxyquinoline and derivatives thereof. The low molecular compound for the charge transport material means a host compound and a charge transport compound used for a low molecular organic electroluminescent device. Specific examples thereof include compounds described in "Organic EL display" (co-authored by Shizuo Tokito, Chihaya Adachi and Hideyuki Murata, Ohmsha, Ltd.) p. 107, Monthly Display (vol. 9, No. 9, 2003, pp. 26-30), JP-A-2004-244400, JP-A-2004-277377, and the like. Although depending on the type of the charge transport material, it is generally preferable for obtaining satisfactory light emission from the metal complex that the lowest triplet excitation energy of the charge transport material is higher than the lowest triplet excitation energy of the metal complex.

Specifically, the low molecular compound for the charge transport material may include compounds below.

[Chem. 15]

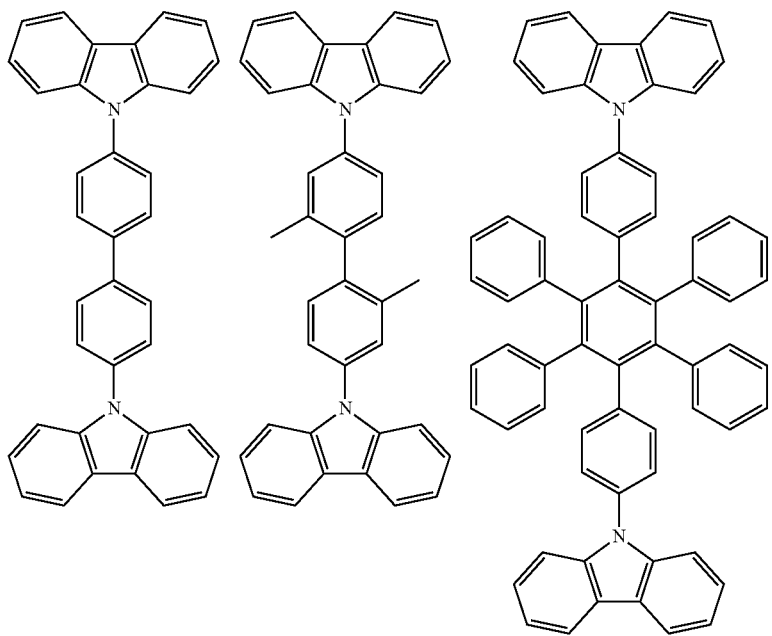

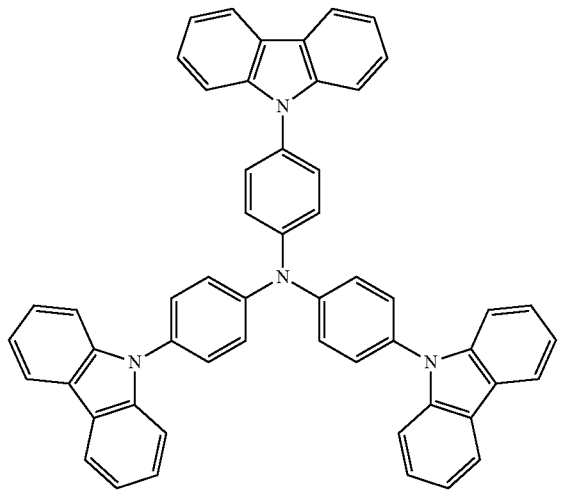

[Chem. 16]
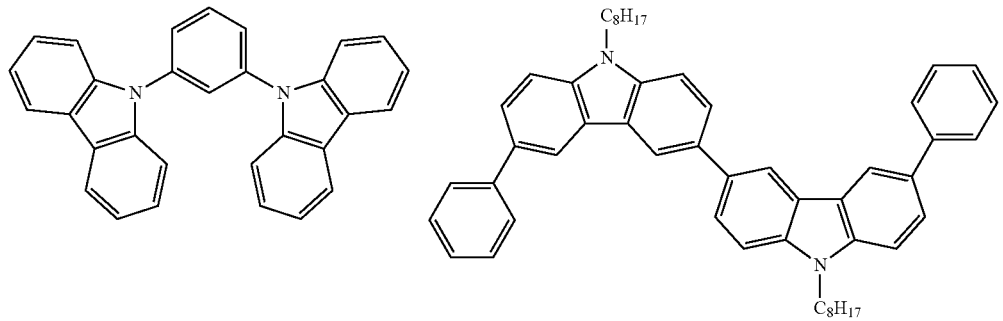
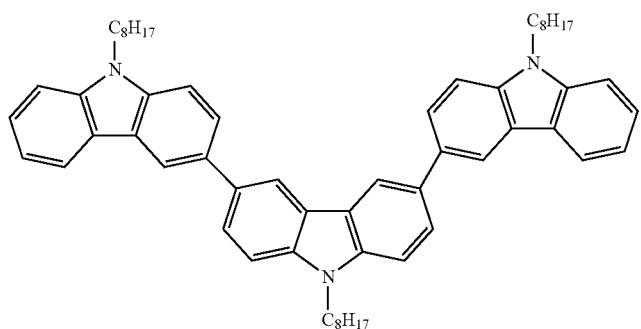
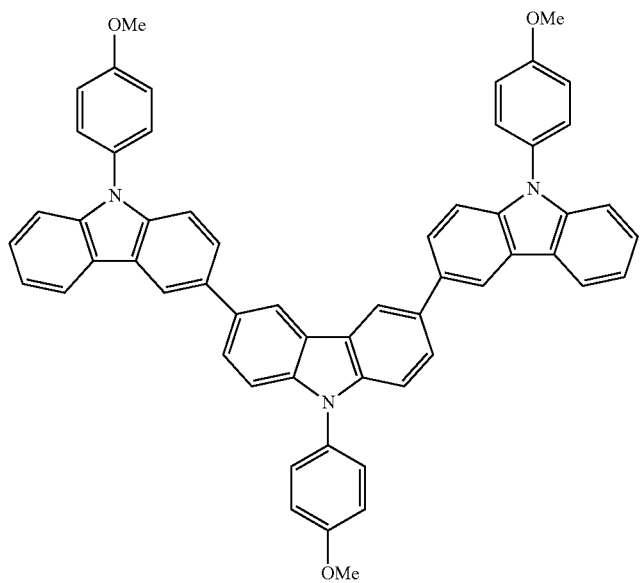

-continued
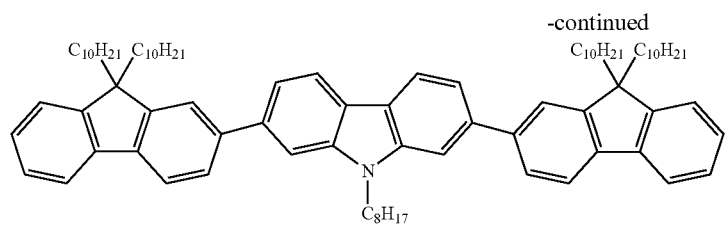
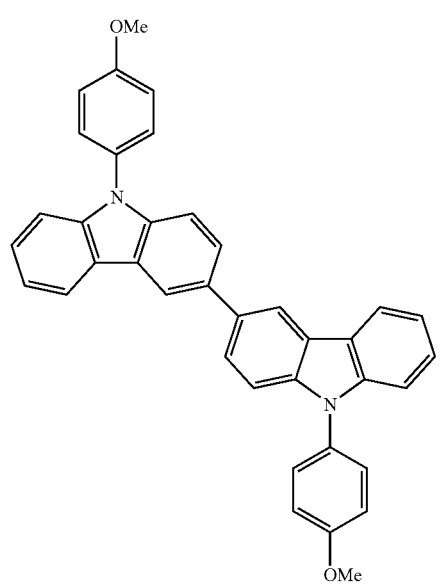
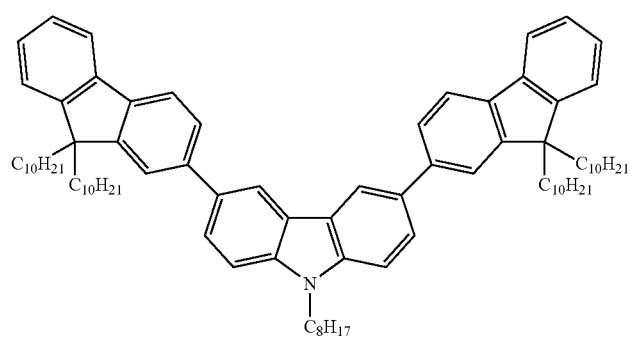
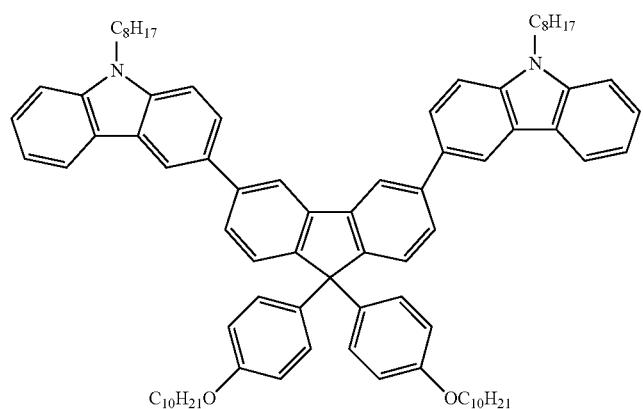
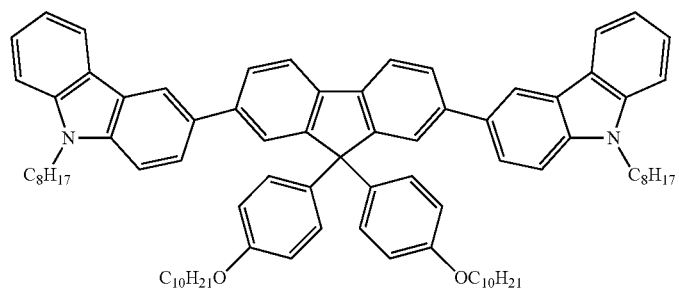

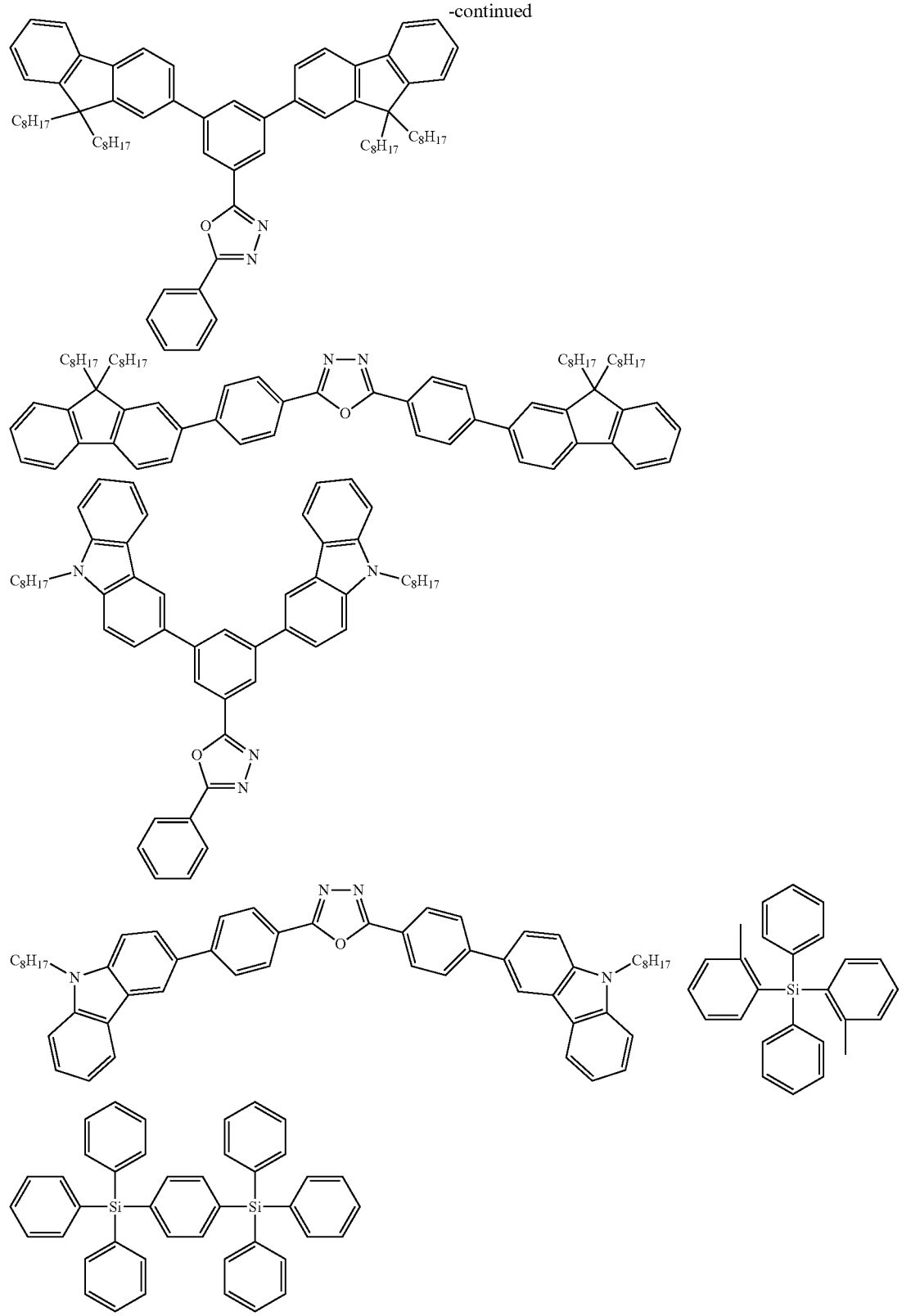

Examples of the polymer compound for the charge transport material include a non-conjugated polymer compound and a conjugated polymer compound. Examples of the non-conjugated polymer compound include polyvinyl carbazole. Examples of the conjugated polymer compound may include polymer compounds containing an aromatic ring in the main chain thereof, such as polymer compounds containing, as a repeating unit in the main chain thereof, a phenylene group optionally having a substituent, a fluorenediyl group optionally having a substituent, a dibenzothiophenediyl group optionally having a substituent, a dibenzofurandiyl group optionally having a substituent, a dibenzosilolediyl group optionally having a substituent or the like; and copolymers of these groups with each other. Specifically, the conjugated polymer compound includes a polymer compound having, as a partial structure of a repeating unit thereof, a benzene ring optionally having a substituent. Other examples thereof include polymer compounds described in, for example, JP-A-2003-231741, JP-A-2004-059899, JP-A-2004-002654, JP-A-2004-292546, U.S. Pat. No. 5,708,130, WO99/54385, WO00/46321, WO02/077060, "Organic EL display" (co-authored by Shizuo Tokito, Chihaya Adachi and Hideyuki Murata, Ohmsha, Ltd.) p. 111, Monthly Display (vol. 9, No. 9, 2002), pp. 47-51, and the like.

The polymer compound for the charge transport material is preferably a polymer compound containing a group represented by Formula (I):

—Ar—           (I)

wherein Ar represents an arylene group, a divalent heterocyclic group or a divalent aromatic amine residue, and these groups may have a substituent.

Examples of the arylene group represented by Ar in Formula (I) include a phenylene group optionally having a substituent, a naphthylene group optionally having a substituent, and a divalent group represented by Formula (4a).

[Chem. 17]

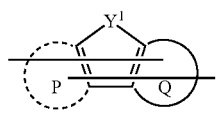

(4a)

In the formula, a ring P and a ring Q each independently represent an aromatic ring, and the ring P may or may not exist. With regard to two bonds, when the ring P exists, two bonds exist on the ring P or the ring Q, or one bond exists on the ring P and another bond exists on the ring Q. When the ring P does not exist, two bonds exist on a 5-membered ring containing $Y^1$ (which may also be a 6-membered ring) or the ring Q, or one bond exists on the 5-membered ring containing $Y^1$ (which may also be a 6-membered ring) and another bond exists on the ring Q. The ring P, the ring Q, and the 5-membered ring containing $Y^1$ (which may also be a 6-membered ring) may each independently have at least one substituent selected from the group consisting of an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group.

$Y^1$ represents $-C(R^{11})(R^{12})-$, $-C(R^{14})(R^{15})-C(R^{16})(R^{17})-$, or $-C(R^{32})=C(R^{33})-$. $R^{11}$, $R^{12}$, $R^{14}$ to $R^{17}$, $R^{32}$ and $R^{33}$ each independently represent a hydrogen atom, an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group or a halogen atom.

In Formula (I), an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group which are substituents that the ring P, the ring Q, and the 5-membered ring containing $Y^1$ (which may also be a 6-membered ring) may have are the same as the groups and atoms described and exemplified above as the groups and atoms represented by R.

In Formula (I), an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group and a halogen atom represented by $R^{11}$, $R^{12}$, $R^{14}$ to $R^{17}$, $R^{32}$ and $R^{33}$ are the same as the groups and atoms described and exemplified above as the groups and atoms represented by R.

In Formula (I), the divalent heterocyclic group represented by Ar refers to an atomic group remaining after removing two hydrogen atoms from a heterocyclic compound, and the group may have a substituent. The heterocyclic compound refers to a compound containing not only a carbon atom but also one or more types of atoms selected from the group consisting of an oxygen atom, a nitrogen atom, a silicon atom, a germanium atom, a tin atom, a phosphorus atom, a boron atom, a sulfur atom, a selenium atom and a tellurium atom as an element constituting the ring, among organic compounds having a cyclic structure. Among divalent heterocyclic groups, a divalent aromatic heterocyclic group is preferred. The divalent heterocyclic group has usually 3 to 60 carbon atoms without the number of carbon atoms of the substituent. The total number of carbon atoms of the divalent heterocyclic group including the number of carbon atoms of the substituent is usually 3 to 100.

Examples of the divalent heterocyclic group represented by Ar in Formula (I) include a divalent group represented by Formula (4b).

[Chem. 18]

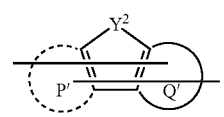

(4b)

In the formula, a ring P' and a ring Q' each independently represent an aromatic ring and the ring P' may or may not exist. With regard to two bonds, when the ring P' exists, two bonds exist on the ring P' or the ring Q', or one bond exists on the ring P' and another bond exists on the ring Q. When the ring P' does not exist, two bonds exist on a 5-membered ring containing $Y^2$ (which may also be the 6-membered ring) or the ring Q', or one bond exists on the 5-membered ring containing Y² (which may also be the 6-membered ring) and another bond exists on the ring Q'. The ring P', the ring Q', and the 5-membered ring containing Y² (which may also be a 6-membered ring) may each independently have at least one substituent selected from the group consisting of an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group.

Y² represents —O—, —S—, —Se—, —B(R⁶)—, —Si (R⁷)(R⁸)—, —P(R⁹)—, —PR¹⁰(=O)—, —N(R¹³)—, —O—C(R¹⁸)(R¹⁹)—, —S—C(R²⁰)(R²¹)—, —N—C(R²²) (R²³)—, —Si(R²⁴)(R²⁵)—C(R²⁶)(R²⁷)—, —Si(R²⁸) (R²⁹)—Si (R³⁰)(R³¹)—, —N=C(R³⁴)—, or —Si(R³⁵)=C (R³⁶)—. R⁶ to R¹⁰, R¹³, R¹⁸ to R³¹ and R³⁴ to R³⁶ each independently represent a hydrogen atom, an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group or a halogen atom.

In the formula, an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group which are substituents that the ring P', the ring Q', and the 5-membered ring containing Y² (which may also be a 6-membered ring) may have are the same as the groups and atoms described and exemplified above as the groups and atoms represented by R.

In the formula, an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a silyloxy group, a substituted silyloxy group, a monovalent heterocyclic group and a halogen atom represented by R⁶ to R¹⁰, R¹³, R¹⁸ to R³¹ and R³⁴ to R³⁶ are the same as the groups and atoms described and exemplified above as the groups and atoms represented by R.

In Formula (I), the divalent aromatic amine residue represented by Ar means an atomic group remaining after removing two hydrogen atoms from an aromatic amine.

The divalent aromatic amine residue has usually 5 to 100 carbon atoms, and preferably 15 to 60 carbon atoms. The number of carbon atoms of the divalent aromatic amine residue does not include the number of carbon atoms of the substituent.

Examples of the divalent aromatic amine residue represented by Ar in Formula (I) include a divalent group represented by Formula (6):

[Chem. 19]

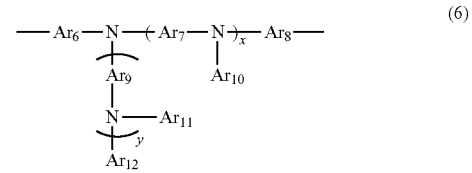

wherein

Ar₆, Ar₇, Ar₈ and Ar₉ each independently represent an arylene group or a divalent heterocyclic group, Ar₁₀, Ar₁₁ and Ar₁₂ each independently represent an aryl group or a monovalent heterocyclic group, Ar₆ to Ar₁₂ may have a substituent; and x and y are each independently 0 or 1.

In Formula (6), the arylene group represented by Ar₆ to Ar₉ is an atomic group remaining after removing two hydrogen atoms from an aromatic hydrocarbon. The arylene group also includes a group having a fused ring and a group in which two or more selected from among an independent benzene ring and a fused ring are bonded with each other either directly or through a group such as a vinylene group. The arylene group may have a substituent. The arylene group has usually 6 to 60 carbon atoms, and preferably 6 to 20 carbon atoms without the number of carbon atoms of the substituent. The total number of carbon atoms of the arylene group including the number of carbon atoms of the substituent is usually 6 to 100.

In Formula (6), the divalent heterocyclic group represented by Ar₆ to Ar₉ is the same as the group described and exemplified above as the divalent heterocyclic group represented by Ar.

In Formula (6), the aryl group and the monovalent heterocyclic group represented by Ar₁₀ to Ar₁₂ are the same as the groups described and exemplified above as the aryl group and the monovalent heterocyclic group represented by R.

In Formula (6), the substituent that the arylene group, the divalent heterocyclic group, the aryl group and the monovalent heterocyclic group may have includes an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group, a cyano group and a nitro group. These substituents are the same as the groups and atoms described and exemplified above as the groups and atoms represented by R.

Examples of the groups represented by Formula (4a) and Formula (4b) include a group represented by Formula (4-1), Formula (4-2) or Formula (4-3):

[Chem. 20]

-continued

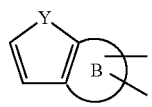
Formula (4-2)

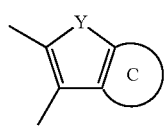
Formula (4-3)

wherein
a ring A, a ring B and a ring C each independently represent an aromatic ring;
Y represents the same meaning as $Y^1$ or the same meaning as $Y^2$;
the ring A, the ring B, the ring C, and a 5-membered ring containing Y (which may also be a 6-membered ring) may each independently have one or more substituents selected from the group consisting of an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amido group, an acid imido group, a monovalent heterocyclic group, a carboxyl group, a substituted carboxyl group and a cyano group; and
a group represented by Formula (4-4) and Formula (4-5):

[Chem. 21]

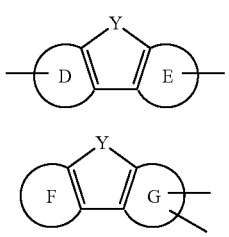

Formula (4-4)

Formula (4-5)

wherein
a ring D, a ring E, a ring F and a ring G each independently represent an aromatic ring;
Y represents the same meaning as $Y^1$ or the same meaning as $Y^2$;
the ring D, the ring E, the ring F, the ring G and a 5-membered ring containing Y (which may also be a 6-membered ring) may each independently have one or more substituents selected from the group consisting of an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, a halogen atom, an acyl group, an acyloxy group, an imine residue, a carbamoyl group, an amino group, an acid imido group, a monovalent heterocyclic group, a carboxyl group, a substituted carboxyl group and a cyano group.
Among them, a group represented by Formula (4-4) or Formula (4-5) is preferred.

In Formula (4-1) to Formula (4-5), Y is preferably —S—, —O—, —C($R^{11}$)($R^{12}$)— or —N($R^{13}$)—, and more preferably —S—, —O— or —N($R^{13}$)— from the viewpoint of the luminous efficiency of the light-emitting device manufactured using the composition of the present invention.

Examples of the aromatic rings in Formulae (4-1) to (4-5) include: aromatic rings such as a benzene ring, a naphthalene ring, an anthracene ring, a tetracene ring, a pentacene ring, a pyrene ring and a phenanthrene ring; and aromatic heterocyclic rings such as a pyridine ring, a bipyridine ring, a phenanthroline ring, a quinoline ring, an isoquinoline ring, a thiophene ring, a furan ring and a pyrrole ring.

As the substituent that the groups represented by Formulae (4-1) to (4-5) may have, preferred is an alkyl group, an alkyloxy group, an alkylthio group, an aryl group, an aryloxy group, an arylthio group, an arylalkyl group, an arylalkyloxy group, an arylalkylthio group, an arylalkenyl group, an arylalkynyl group, an amino group, a substituted amino group, a silyl group, a substituted silyl group, an acyloxy group, an imine residue, a carbamoyl group, an amido group, an acid imido group, a monovalent heterocyclic group, a carboxyl group and a substituted carboxyl group, and more preferred is an alkyl group, an alkyloxy group, an aryl group and a monovalent heterocyclic group.

The polymer compound for the charge transport material is, for example, a polymer compound containing a group among the following (that is, a group in parentheses in the following examples), and particularly preferably a polymer compound containing a group among the following as a repeating unit.

[Chem. 22]

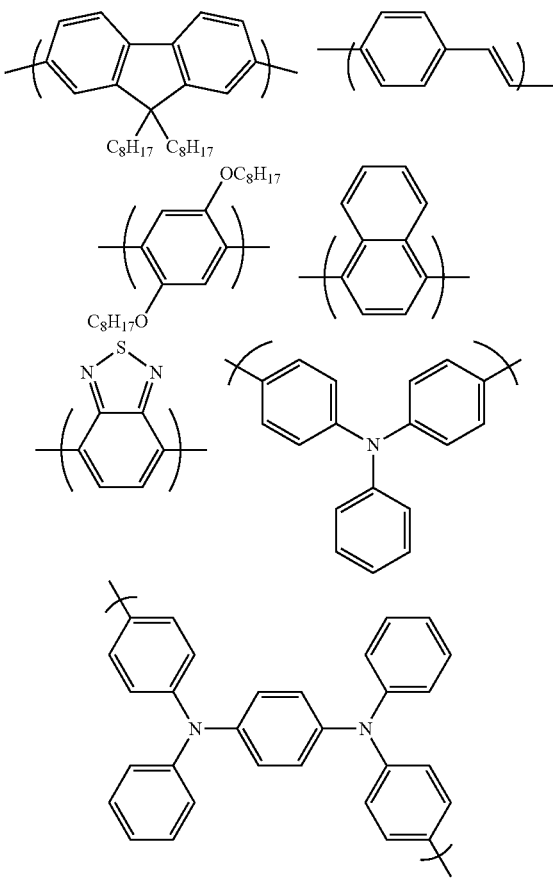

-continued

[Chemical structures shown: dibenzofuran with C8H17O and OC8H17 substituents; dibenzothiophene analog; thiophene repeat unit; dibenzosilole with C8H17O/OC8H17 and C8H17 groups on Si; a chromene/pyran-type structure with C8H17 groups; a fluorene-naphthalene fused structure with C8H17 groups; a carbazole with N-phenyl-OC5H11 group; another carbazole with N-phenyl-OC5H11 group]

The lowest triplet excitation energy of the low molecular compound or polymer compound for the charge transport material (TH) and the lowest triplet excitation energy of the metal complex of the present invention (TM) satisfy: preferably a relation of $$TH > TM - 0.1 \text{ (eV)};$$

more preferably a relation of $$TH > TM; \text{ and}$$

further preferably a relation of $$TH > TM + 0.1 \text{ (eV)}.$$

When using the polymer compound for the charge transport material, the polymer compound has a polystyrene-equivalent number average molecular weight of preferably $10^3$ to $10^8$, and more preferably $10^4$ to $10^6$. The polymer compound has a polystyrene-equivalent weight average molecular weight of preferably $10^3$ to $10^8$, and more preferably $5 \times 10^4$ to $5 \times 10^6$.

For the light-emitting material, a publicly known light-emitting material can be used. Examples thereof include low molecular light-emitting materials such as naphthalene derivatives; anthracene and derivatives thereof; perylene and derivatives thereof; dyes such as polymethine-based, xanthene-based, coumarin-based and cyanine-based dyes; metal complexes of 8-hydroxyquinoline and derivatives thereof; aromatic amines; tetraphenylcyclopentadiene and derivatives thereof; and tetraphenylbutadiene and derivatives thereof.

The amount of the metal complex of the present invention in the composition of the present invention is usually 0.1 to 80 parts by weight, preferably 0.1 to 60 parts by weight, and more preferably 0.1 to 40 parts by weight, when the total amount of the composition of the present invention is defined as 100 parts by weight. The metal complexes of the present invention may be used alone or in combination of two or more types thereof.

<Light-Emitting Device>

One embodiment of the light-emitting device of the present invention is a device including: a pair of electrodes composed of an anode and a cathode; and a film composed of a single layer (monolayer type) or a plurality of layers (multilayer type) sandwiched between the electrodes, wherein the film includes at least a light-emitting layer. At least one layer of the film layer contains the metal complex of the present invention. The content of the metal complex of the present invention in the film is usually 0.1 to 100% by weight, preferably 0.1 to 80% by weight, more preferably 0.1 to 60% by weight, and further preferably 0.1 to 40% by weight, based on the total weight of the light-emitting layer. In the light-emitting device of the present invention, it is preferable that the light-emitting layer contains the metal complex of the present invention as the light-emitting material.

When the light-emitting device of the present invention is of the monolayer type, the film is the light-emitting layer and the light-emitting layer contains the metal complex of the present invention. When the light-emitting device of the present invention is of the monolayer type or the multilayer type, the light-emitting device takes, for example, the following layer configurations:

a) Anode/Light-emitting layer/Cathode
b) Anode/Hole transport layer/Light-emitting layer/Cathode
c) Anode/Light-emitting layer/Electron transport layer/Cathode
d) Anode/Hole transport layer/Light-emitting layer/Electron transport layer/Cathode
e) Anode/Charge injection layer/Light-emitting layer/Cathode
f) Anode/Light-emitting layer/Charge injection layer/Cathode
g) Anode/Charge injection layer/Light-emitting layer/Charge injection layer/Cathode
h) Anode/Charge injection layer/Hole transport layer/Light-emitting layer/Cathode i) Anode/Hole transport layer/Light-emitting layer/Charge injection layer/Cathode
j) Anode/Charge injection layer/Hole transport layer/Light-emitting layer/Charge injection layer/Cathode
k) Anode/Charge injection layer/Light-emitting layer/Charge transport layer/Cathode
l) Anode/Light-emitting layer/Electron transport layer/Charge injection layer/Cathode
m) Anode/Charge injection layer/Light-emitting layer/Electron transport layer/Charge injection layer/Cathode
n) Anode/Charge injection layer/Hole transport layer/Light-emitting layer/Charge transport layer/Cathode
o) Anode/Hole transport layer/Light-emitting layer/Electron transport layer/Charge injection layer/Cathode
p) Anode/Charge injection layer/Hole transport layer/Light-emitting layer/Electron transport layer/Charge injection layer/Cathode The symbol "/" indicates that the layers are stacked adjacent to each other. The same shall apply hereinafter.

The anode of the light-emitting device of the present invention is an electrode for supplying holes to the hole injection layer, the hole transport layer, the light-emitting layer, and the like. It is effective that the anode has a work function of 4.5 eV or more. As a material for the anode, a metal, an alloy, a metal oxide, an electroconductive compound, a mixture thereof, and the like can be used. Specifically, the material includes: conductive metal oxides such as tin oxide, zinc oxide, indium oxide and indium-tin-oxide (ITO); metals such as gold, silver, chromium and nickel; a mixture or a layered product of the conductive metal oxide and the metal; inorganic conductive substances such as copper iodide and copper sulfide; organic conductive materials such as polyanilines, polythiophenes (such as PEDOT), and polypyrroles; and a layered product of these with ITO.

The cathode of the light-emitting device of the present invention is an electrode for supplying electrons to the electron injection layer, the electron transport layer, the light-emitting layer, and the like. As a material for the cathode, a metal, an alloy, a metal halide, a metal oxide, an electroconductive compound, and a mixture thereof can be used. Examples of the material for the cathode include alkali metals (such as lithium, sodium and potassium) and fluorides and oxides thereof; alkaline earth metals (such as magnesium, calcium, barium and cesium) and fluorides and oxides thereof; gold, silver, lead, aluminum, and alloys and mixed metals (such as a sodium-potassium alloy, a sodium-potassium mixed metal, a lithium-aluminum alloy, a lithium-aluminum mixed metal, a magnesium-silver alloy and a magnesium-silver mixed metal); and rare-earth metals (such as indium and ytterbium).

The hole injection layer and the hole transport layer of the light-emitting device of the present invention are layers that have only to have any one of a function of injecting holes from the anode, a function of transporting holes, and a function of blocking electrons injected from the cathode. As a material for these layers, a publicly known material can be appropriately selected and used. Examples thereof include carbazole derivatives, triazole derivatives, oxazole derivatives, oxadiazole derivatives, imidazole derivatives, polyaryl alkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, polysilane-based compounds, poly(N-vinylcarbazole) derivatives, organic silane derivatives, the metal complex of the present invention, and polymers containing these compounds. Other examples thereof include: aniline-based copolymers; and conductive polymers and oligomers such as thiophene oligomer and polythiophene. These materials may be used alone or in combination of two or more types thereof. The hole injection layer and the hole transport layer may have either a monolayer structure composed of one type or two or more types of the above materials or a multilayer structure composed of a plurality of layers having the same composition or different compositions.

The electron injection layer and the electron transport layer of the light-emitting device of the present invention are layers that have only to have any one of a function of injecting electrons from the cathode, a function of transporting electrons, and a function of blocking holes injected from the anode. As a material for these layers, a publicly known material can be appropriately selected and used. Examples thereof include: triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidene methane derivatives, distyrylpyrazine derivatives, tetracarboxylic anhydrides of aromatic ring such as naphthalene and perylene, phthalocyanine derivatives, various metal complexes typified by metal complexes of 8-quinolinol derivatives, metal phthalocyanines and a metal complex having benzoxazole or benzothiazole as a ligand, organic silane derivatives, and the metal complex of the present invention. The electron injection layer and the electron transport layer may have either a monolayer structure composed of one type or two or more types of the above materials or a multilayer structure composed of a plurality of layers having the same composition or different compositions.

In the light-emitting device of the present invention, an inorganic compound that is an insulator or a semiconductor can also be used as the material for the electron injection layer and the electron transport layer. When the electron injection layer and the electron transport layer are formed of an insulator or a semiconductor, a leak of current can be effectively prevented to enhance electron injecting property. For such insulator, there can be used at least one metal compound selected from the group consisting of alkali metal chalcogenides, alkaline earth metal chalcogenides, alkali metal halides and alkaline earth metal halides. Preferred examples of alkali metal chalcogenides include CaO, BaO, SrO, BeO, BaS and CaSe. The semiconductor that constitutes the electron injection layer and the electron transport layer includes oxides, nitrides and oxide-nitrides containing at least one element selected from the group consisting of Ba, Ca, Sr, Yb, Al, Ga, In, Li, Na, Cd, Mg, Si, Ta, Sb and Zn. These oxides, nitrides and oxide-nitrides may be used alone or in combination of two or more types thereof.

In the present invention, a reductive dopant may be added to an interface region between the cathode and a film in contact with the cathode. The reductive dopant is preferably at least one compound selected from the group consisting of alkali metals, oxides of alkaline earth metals, alkaline earth metals, rare-earth metals, oxides of alkali metals, halides of alkali metals, oxides of alkaline earth metals, halides of alkaline earth metals, oxides of rare-earth metals, halides of rare-earth metals, complexes of alkali metals, complexes of alkaline earth metals and complexes of rare-earth metals.

The light-emitting layer of the light-emitting device of the present invention is a layer having a function of capable of injecting holes from the anode, the hole injection layer or the hole transport layer and capable of injecting electrons from the cathode, the electron injection layer or the electron transport layer when the electric field is applied; a function of moving the injected charges (electrons and holes) by the force of the electric field; and a function of providing a site where electrons and holes are recombined and thereby leading to light emission. The light-emitting layer of the light-emitting device of the present invention preferably contains the metal complex of the present invention, and may also contain a host material such that the metal complex serves as a guest material. The host material includes the charge transport materials noted above. A light-emitting layer in which the light-emitting material is doped in the host material can be formed by mixing the host material and the light-emitting material such as the metal complex and applying the mixture, or by conducting co-evaporation of the host material and the light-emitting material.

In the light-emitting device of the present invention, the method for forming each of the layers is not particularly limited and publicly known methods can be used. Specifically, the method includes a vacuum deposition method (such as a resistance heating deposition method and an electron beam method), a sputtering method, an LB method, a molecule layering method, and an application method (such as a casting method, a spin coating method, a bar coating method, a blade coating method, a roll coating method, a gravure printing method, a screen printing method and an inkjet method). Among them, the application method is preferred for forming a film because the manufacturing step could be simplified. In the application method, each layer can be formed by: dissolving the metal complex of the present invention into a solvent to prepare an applying liquid; applying the applying liquid onto a desired layer (or electrode); and drying the liquid. The applying liquid may contain a resin as a host material and/or a binder. The resin may be present in a solvent either in a dissolved state or in a dispersed state. Depending on purposes, the resin can be selected from among, for example, polyvinyl chloride, a polycarbonate, polystyrene, polymethyl methacrylate, polybutyl methacrylate, a polyester, a polysulfone, polyphenylene oxide, polybutadiene, poly(N-vinylcarbazole), a hydrocarbon resin, a ketone resin, a phenyloxy resin, a polyamide, ethyl cellulose, vinyl acetate, an ABS resin, polyurethane, a melamine resin, an unsaturated polyester resin, an alkyd resin, an epoxy resin, a silicone resin, and the like. Depending on purposes, the solution may contain an antioxidant, a viscosity control agent, and the like as an optional component.

<Photoelectric Device>

The metal complex of the present invention can be used for the manufacture of a photoelectric device.

Examples of the photoelectric device include a photoelectric conversion device, specifically, a device in which a layer containing the metal complex of the present invention is provided between two electrodes at least one of which is transparent or semi-transparent, a device in which an interdigital electrode is formed on a layer that contains the metal complex of the present invention and that is provided as a film on a substrate. For enhancing the characteristics, there may be blended fullerene, carbon nanotube, and the like.

The method for manufacturing the photoelectric conversion device includes a method disclosed in Japanese Patent No. 3146296. Specific examples thereof include a method that involves forming a layer (film) containing the metal complex of the present invention on a substrate having a first electrode and forming a second electrode on the layer, and a method that involves forming a layer (film) containing the metal complex of the present invention on a pair of interdigital electrodes formed on a substrate. Either of the first electrode or the second electrode is transparent or semi-transparent.

Although the method for forming the layer (film) containing the metal complex of the present invention and the method for blending fullerene or carbon nanotube are not particularly limited, the methods shown as an example with respect to the light-emitting device can be suitably used.

<Liquid Composition>

The liquid composition of the present invention comprises the metal complex of the present invention and a solvent or dispersion medium. As the solvent or dispersion medium used for the liquid composition of the present invention, a solvent or dispersion medium that is capable of homogeneously dissolving or dispersing the component of the film and that is stable can be appropriately selected for use from publicly known solvents. Such a solvent includes chlorine-based solvents (such as chloroform, methylene chloride, 1,2-dichloroethane, 1,1,2-trichloroethane, chlorobenzene and o-dichlorobenzene), ether solvents (such as tetrahydrofuran and dioxane), aromatic hydrocarbon solvents (such as benzene, toluene and xylene), aliphatic hydrocarbon solvents (such as cyclohexane, methylcyclohexane, n-pentane, n-hexane, n-heptane, n-octane, n-nonane and n-decane), ketone solvents (such as acetone, methyl ethyl ketone and cyclohexanone), ester solvents (such as ethyl acetate, butyl acetate and ethylcellosolve acetate), polyhydric alcohols and derivatives thereof (such as ethylene glycol, ethylene glycol monobutyl ether, ethylene glycol monoethyl ether, ethylene glycol monomethyl ether, di(methyloxy)ethane, propylene glycol, di(ethyloxy)methane, triethylene glycol monoethyl ether, glycerin and 1,2-hexanediol), alcohol solvents (such as methanol, ethanol, propanol, isopropanol and cyclohexanol), sulfoxide solvents (such as dimethylsulfoxide), and amide solvents (such as N-methyl-2-pyrrolidone and N,N-dimethylformamide). These solvents may be used alone or in combination of two or more types thereof.

When the liquid composition is applied to an inkjet method, the liquid composition may comprise a publicly known additive for favorable discharge properties of the liquid composition and reproducibility thereof. The publicly known additive includes a solvent having a high boiling point (such as anisole and bicyclohexylbenzene) for suppressing evaporation through a nozzle. The liquid composition comprising the publicly known additive preferably has a viscosity at 25° C. of 1 to 100 mPa·s.

A preferred thickness of each layer of the light-emitting device of the present invention varies depending on the type of material and the layer configuration and is not particularly limited. Generally, too small thickness of layer tends to cause a defect such as a pinhole and too large thickness requires a high applied voltage, leading to low luminous efficiency. Thus, it is usually preferable that the thickness is from several nm to 1 μm.

The use application of the light-emitting device of the present invention includes, but is not particularly limited to, a planar light source, a light source for illumination apparatus (or a light source), a light source for a signal, a light source for a backlight, a display device, a printer head, and the like. In the display device, configurations such as a segment-type and a dot matrix-type can be selected by using a publicly known driving technology, driving circuit, and the like.

<Other use Applications>

The metal complex of the present invention is not only useful for the manufacture of the light-emitting device, but also can be used, for example, as a semiconductor material such as an organic semiconductor material, a light-emitting material, an optical material and a conductive material (for example, the metal complex is applied by doping). Accordingly, the metal complex can be used to manufacture a film (that is, a film containing the metal complex) such as a light-emitting film, a conductive film and an organic semiconductor film.

The metal complex of the present invention can be formed into a conductive film and a semiconductor film by the same method as the method for manufacturing a light-emitting film used for the light-emitting layer of the light-emitting device. Either larger one of the electron mobility or the hole mobility of the semiconductor film is preferably $10^{-5}$ cm$^2$/V/sec or more. The organic semiconductor film can be suitably used for an organic solar cell, an organic transistor, and the like.

EXAMPLES

The present invention will be described in more detail below with reference to Examples, but it should not be construed that the present invention is limited to these Examples.

Example 1

Synthesis of Compound (MC-1)

[Chem. 23]

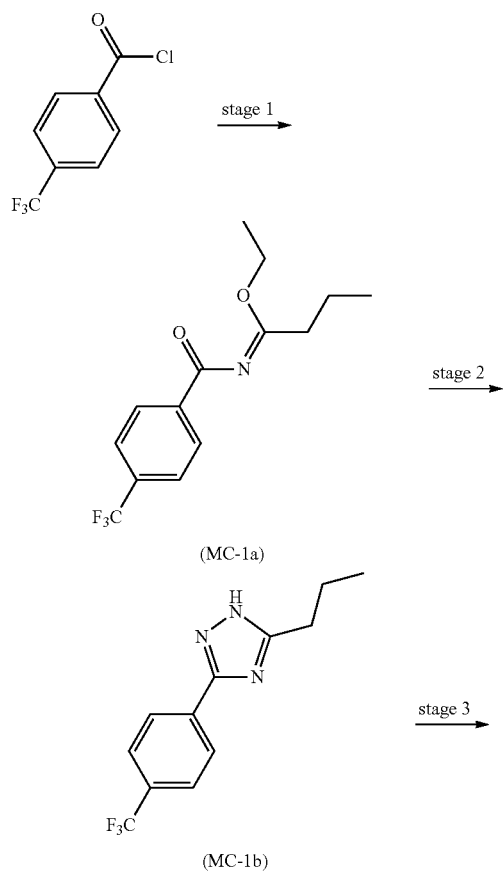

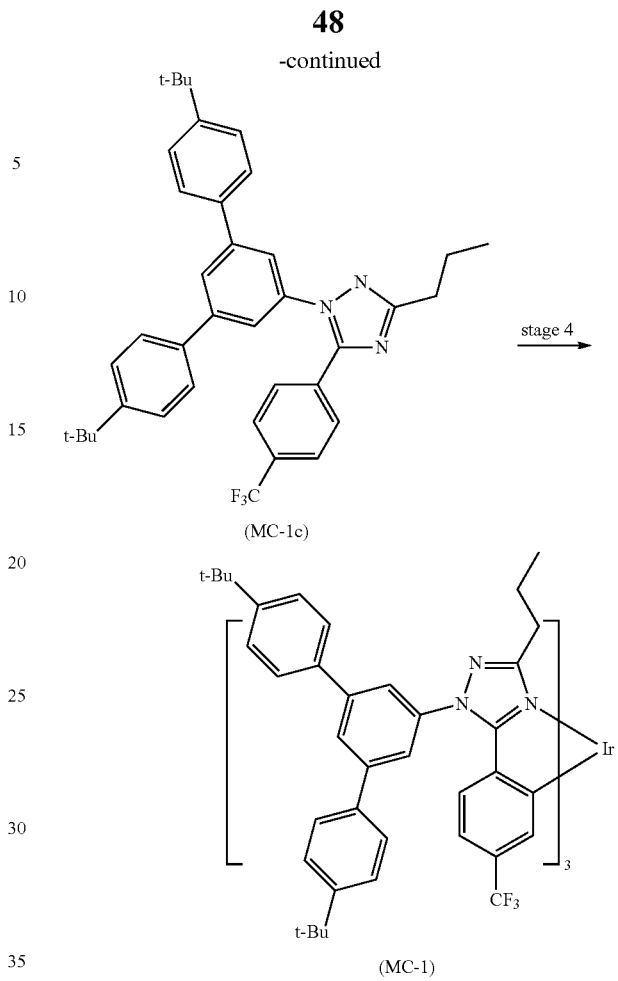

<Stage 1>

Six point two (6.2) grams (30 mmol) of 4-trifluoromethylbenzoyl chloride and 4.5 g (30 mmol) of ethyl butyrimidate hydrochloride were weighed and were dissolved in 300 mL of chloroform, and the resultant was placed under a nitrogen atmosphere. Thereafter, 25 mL of a chloroform solution of 8.4 mL (60 mmol) of triethylamine was added dropwise thereto and the resultant was stirred at room temperature under a nitrogen atmosphere. After 15 hours, chloroform as a solvent was concentrated and the concentrate was suspended in 200 mL of water, followed by extracting the resultant with dichloromethane. The resultant solution was concentrated under reduced pressure, thus obtaining 8.0 g (28 mmol) of a compound (MC-1a) as a light yellow liquid.

<Stage 2>

Into 60 mL of chloroform, 3.0 g (10 mmol) of the compound (MC-1a) was dissolved and the resultant was placed under a nitrogen atmosphere. Thereto, 0.55 mL (11 mmol) of hydrazine hydrate was added dropwise under a nitrogen atmosphere at room temperature. After the dropwise addition, the resultant was stirred under a nitrogen atmosphere at room temperature for 17 hours and then 50 mL of water was added therein to quench the reaction. The reaction liquid was transferred into a separating funnel and was washed with water, followed by recovering and concentrating an oil layer. The obtained crude product was recrystallized from a mixed solvent of toluene-hexane, thus obtaining 2.1 g of a compound (MC-1b) as a white solid in a yield of 82%. The result of the $^1$H-NMR analysis is shown below:

¹H-NMR (400 MHz/CDCl₃): δ (ppm) 8.15 (d, 2H), 7.66 (d, 2H), 2.78 (t, 2H), 1.82 (hex, 2H), 0.94 (t, 3H).

<stage 3>

Twenty (20) grams (80 mmol) of the compound (MC-1b), 41 g (107 mmol) of 3,5-di(4-tert-butylphenyl)phenylboronic acid, 24.4 g (135 mmol) of copper(II) acetate, and 50 g of 3A molecular sieves (manufactured by Wako Pure Chemical Industries, Ltd.) were weighed, and thereto, 1 L of dichloromethane and 50 mL of pyridine were added. The resultant was stirred at room temperature for 60 hours. After 60 hours, the suspension was subjected to suction filtration and then washed with 500 mL of dichloromethane. The filtrate was concentrated and then dissolved in dichloromethane, followed by washing the resultant with 300 mL of water several times. The oil layer was dried and passed through a silica gel column to be separated and purified using a mixed solvent of dichloromethane-hexane. The obtained compound was recrystallized from a mixed solvent of methanol-tetrahydrofuran, thus obtaining 2.2 g (3.7 mmol) of a compound (MC-1c) as a pale yellow solid. The result of the ¹H-NMR analysis is shown below:

¹H-NMR (400 MHz/((CD₃)₂CO): δ (ppm) 7.99 (t, 1H), 7.86 (d, 2H), 7.79 (d, 2H), 7.62 (d, 2H), 7.60 (ddd, 4H), 7.50 (ddd, 4H), 2.78 (t, 2H), 1.87 (td, 2H), 1.34 (s, 18H), 1.06 (t, 3H).

<stage 4>

One hundred forty (140) milligrams (0.4 mmol) of iridium chloride and 600 mg (1.0 mmol) of the compound (MC-1c) were weighed, and thereto, 3 mL of water and 9 mL of 2-butoxyethanol were added, followed by placing the resultant under an argon atmosphere and heating and refluxing for 15 hours. After cooling down, the reaction liquid was concentrated under reduced pressure. The residue was dissolved in dichloromethane and then washed with water. The oil layer was concentrated, dried, and recrystallized from a mixed solvent of dichloromethane-hexane to obtain 680 mg of a yellow solid powder. Then, 680 mg of the yellow solid powder and 1.23 g (2.1 mmol) of the compound (MC-1c) were weighed, and thereto, 120 mg (0.47 mmol) of silver trifluoromethanesulfonate was added under an argon atmosphere, and then 3 mL of diethylene glycol dimethyl ester was added. Thereafter, the resultant was heated and refluxed for 24 hours in an argon atmosphere and was left to be cooled down. To the reaction mixture, 20 mL of dichloromethane was added and the resultant was subjected to suction filtration. The filtrate was concentrated and dried. The resultant crude product was passed through a silica gel column to be separated and purified using a mixed solvent of dichloromethane-hexane. The eluate was concentrated and the resultant was recrystallized from a mixed solvent of methanol-tetrahydrofuran and then recrystallized from a mixed solvent of dichloromethane-hexane, thus obtaining 710 mg (0.36 mmol) of a compound (MC-1) [fac-tris(1-(3,5-di(4-tert-butylphenyl)phenyl)-3-propyl-5-(4-trifluoromethylphenyl)-1H-[1,2,4]-triazolato-N,C2') iridium (III)] as a light yellow crystal in a yield of 90%. The result of the ¹H-NMR analysis is shown below:

¹H-NMR (400 MHz/CDCl₃): δ (ppm) 8.04 (dd, 3H), 7.65 (d, 6H), 7.61 (d, 12H), 7.50 (d, 12H), 7.07 (d, 3H), 6.94 (d, 3H), 6.84 (s, 3H), 2.49 (hep, 3H), 2.27 (hep, 3H), 1.69-1.56 (m, 3H), 1.52-1.38 (m, 3H), 1.37 (s, 54H), 0.88 (t, 9H).

Example 2

Synthesis of Compound (MC-2)

[Chem. 24]

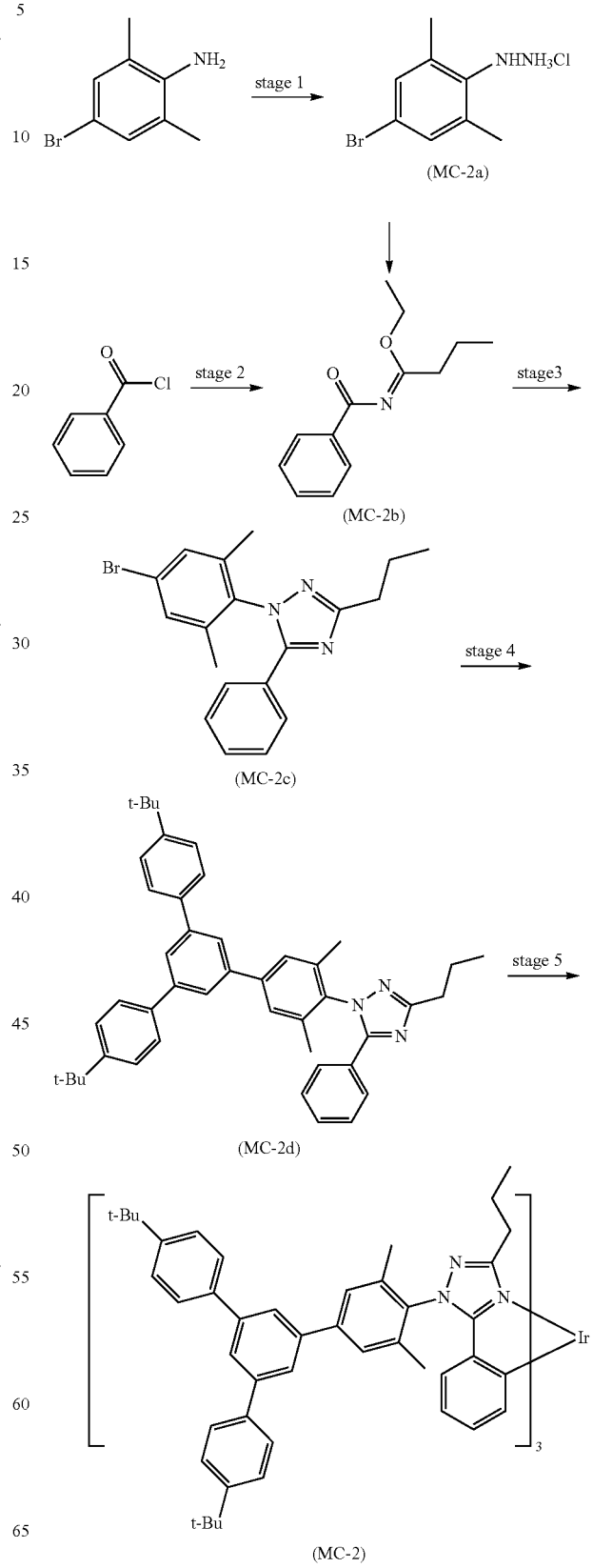

<Stage 1>

Under a nitrogen atmosphere, 1.38 g (20 mmol) of sodium nitrite was dissolved in 11 mL of water of 0° C. Then, 4.0 g (20 mmol) of 4-bromo-2,6-dimethylaniline was suspended in 33 mL of concentrated hydrochloric acid (manufactured by Wako Pure Chemical Industries, Ltd., hydrochloric acid concentration 35 to 37%) and the suspension was added dropwise into the aqueous solution of sodium nitrite at a temperature in a range of not more than 5° C. The resultant was stirred at 0° C. for 15 minutes, and then 15 mL of a concentrated hydrochloric acid solution of 5.31 g (28 mmol) of tin(II) chloride was added to the reaction liquid. The resultant was returned to room temperature and then stirred for 6 hours. The obtained suspension was subjected to suction filtration and was washed with concentrated hydrochloric acid and cold water. The resultant was vacuum-dried, thus obtaining 4.98 g of a compound (MC-2a) as a milky white solid.

<Stage 2>

Three (3) milliliters (26 mmol) of benzoyl chloride and 3.9 g (26 mmol) of ethyl butyrimidate hydrochloride were weighed and were dissolved in 300 mL of chloroform, and the resultant was placed under a nitrogen atmosphere. Thereafter, 25 mL of a chloroform solution of 7.2 mL (52 mmol) of triethylamine was added dropwise thereto and the resultant was stirred under a nitrogen atmosphere at room temperature. After 15 hours, chloroform as a solvent was concentrated and the concentrate was suspended in 200 mL of water, followed by extracting the resultant with dichloromethane. The resultant solution was concentrated under reduced pressure, thus obtaining 5.3 g (24 mmol) of a compound (MC-2b) as a light yellow liquid.

<Stage 3>

Two point four (2.4) grams (9.6 mmol) of the compound (MC-2a), 2.2 g (10 mmol) of the compound (MC-2b), and 800 mg (9.7 mmol) of sodium acetate were weighed, and thereto, 15 mL of acetic acid and 15 mL of dioxane were added, followed by placing the resultant under a nitrogen atmosphere. The reaction mixture was heated at 90° C. for 15 hours and was left to be cooled down. Thereafter, water and ethyl acetate were added thereto to wash the mixture with water and the oil layer was recovered. The resultant crude product was passed through a silica gel column to be separated and purified using a mixed solvent of hexane-ethyl acetate, thus obtaining 1.2 g (3.2 mmol) of a compound (MC-2c) as a light yellow solid in a yield of 33%.

<Stage 4>

1.2 g (3.2 mmol) of the compound (MC-2c), 1.7 g (3.6 mmol) of 3,5-di(4-tert-butylphenyl)phenylboronic acid pinacol ester, 690 mg (6.5 mmol) of sodium carbonate, and 190 mg of tetrakistriphenylphosphino palladium(0) were weighed, and thereto, 8 mL of water and 8 mL of dioxane were added, followed by placing the resultant under a nitrogen atmosphere. The reaction mixture was heated and refluxed for 10 hours and was left to be cooled down. The reaction liquid was concentrated and thereto, water and dichloromethane were added to wash the concentrate with water. Then, the oil layer was recovered and concentrated. The resultant was recrystallized from a mixed solvent of methanol-dichloromethane, thus obtaining 1.1 g (1.7 mmol) of a compound (MC-2d) as white powder in a yield of 51%. The result of the $^1$H-NMR analysis is shown below:

$^1$H-NMR (400 MHz/((CD$_3$)$_2$CO): δ (ppm) 7.92 (d, 2H), 7.89 (tt, 1H), 7.75-7.74 (m, 6H), 7.58-7.52 (m, 6H), 7.40-7.31 (m, 3H), 2.76 (t, 2H), 2.04 (s, 6H), 1.85 (td, 2H), 1.36 (s, 18H), 1.01 (t, 3H).

<Stage 5>

To 88 mg (0.25 mmol) of iridium chloride and 390 mg (0.63 mmol) of the compound (MC-2d), 4 mL of water and 8 mL of 2-butoxyethanol were added, and the resultant was placed under a nitrogen atmosphere. The mixture was heated and refluxed for 15 hours and was left to be cooled down. The reaction liquid was concentrated and thereto, dichloromethane and water were added to wash the concentrate with water. The oil layer was recovered and concentrated to obtain 430 mg of a brown solid. Then, 430 mg of the brown solid, 670 mg (1.1 mmol) of the compound (MC-2d), and 64 mg (0.25 mmol) of silver trifluoromethanesulfonate were weighed and thereto, 1 mL of diethylene glycol dimethyl ester was added, followed by heating and refluxing the resultant for 15 hours under an argon atmosphere. After cooling down, dichloromethane was added thereto and the resultant was subjected to suction filtration, followed by concentrating and drying the filtrate. The obtained crude product was dissolved in dichloromethane and then passed through a silica gel column to be separated and purified using a mixed solvent of dichloromethane-hexane. The obtained eluate was concentrated and the resultant was recrystallized from a mixed solvent of dichloromethane-hexane and then recrystallized from a mixed solvent of dichloromethane-ethanol, thus obtaining 320 mg (0.15 mmol) of a compound (MC-2)[fac-tris(1-(4-(3,5-di(4-tert-butylphenyl)phenyl)-2,6-dimethylphenyl)-3-propyl-5-phenyl-1H-[1,2,4]-triazolato-N,C2') iridium (III)] as light yellow powder in a yield of 61%. The result of the $^1$H-NMR analysis is shown below:

$^1$H-NMR (400 MHz/CD$_2$Cl$_2$): δ (ppm) 7.79 (d, 6H), 7.77 (t, 3H), 7.62 (dt, 12H), 7.59 (s, 3H), 7.51 (s, 3H), 7.47-7.44 (m, 12H), 6.61-6.47 (m, 12H), 2.43 (dt, 3H), 2.30-2.22 (m, 12H), 1.82 (s, 9H), 1.65 (td, 6H), 1.30 (s, 54H), 0.80 (t, 9H).

Example 3

Synthesis of Compound (MC-3)

[Chem. 25]

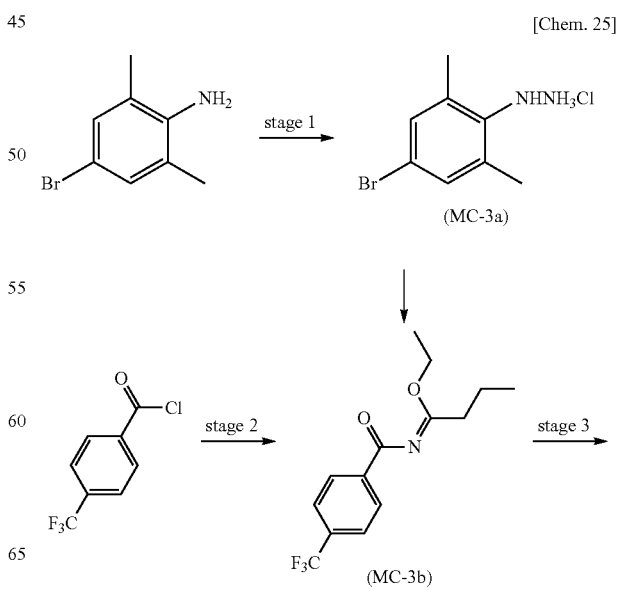

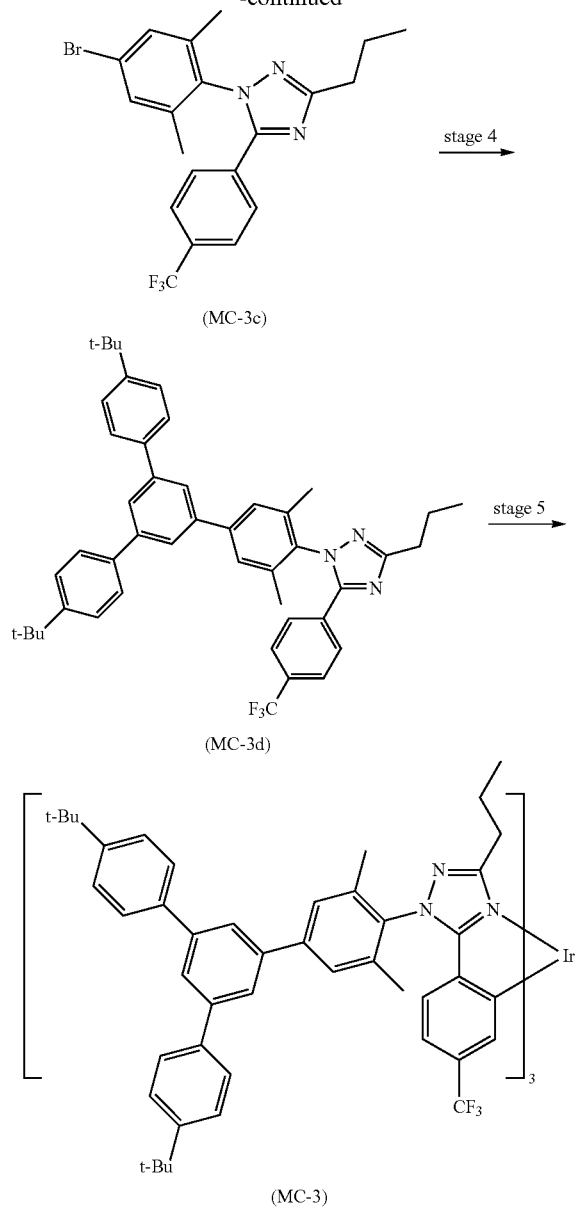

(MC-3c)

(MC-3d)

(MC-3)

<Stage 1>

Under a nitrogen atmosphere, 1.38 g (20 mmol) of sodium nitrite was dissolved in 11 mL of water, and the resultant was placed on an ice bath and was cooled to 0° C. Then, 4.0 g (20 mmol) of 4-bromo-2,6-dimethylaniline was suspended in 33 mL of concentrated hydrochloric acid (manufactured by Wako Pure Chemical Industries, Ltd., hydrochloric acid concentration 35 to 37%) and the suspension was added dropwise into the aqueous solution of sodium nitrite at a temperature in a range of not more than 5° C. The resultant was stirred at 0° C. for 15 minutes and 15 mL of a concentrated hydrochloric acid solution of 5.31 g (28 mmol) of tin(II) chloride was added to the reaction liquid. The resultant was returned to room temperature and then stirred for 6 hours. The obtained suspension was subjected to suction filtration and was washed with concentrated hydrochloric acid and cold water. The resultant was vacuum-dried, thus obtaining 4.98 g of a compound (MC-3a) as a milky white solid.

<Stage 2>

Six point two (6.2) grams (30 mmol) of 4-trifluoromethylbenzoyl chloride and 4.5 g (30 mmol) of ethyl butyrimidate hydrochloride were weighed and were dissolved in 300 mL of chloroform, and the resultant was placed under a nitrogen atmosphere. Thereafter, 25 mL of a chloroform solution of 8.4 mL (60 mmol) of triethylamine was added dropwise thereto and the resultant was stirred under a nitrogen atmosphere at room temperature. After 15 hours, chloroform as a solvent was concentrated and the concentrate was suspended in 200 mL of water, followed by extracting the resultant with dichloromethane. The resultant solution was concentrated under reduced pressure, thus obtaining 8.0 g (28 mmol) of a compound (MC-3b) as a light yellow liquid.

<Stage 3>

Two point six five (2.65) grams (10.6 mmol) of the compound (MC-3a), 2.5 g (8.8 mmol) of the compound (MC-3b), and 870 mg (10.6 mmol) of sodium acetate were weighed, and thereto, 15 mL of acetic acid and 15 mL of dioxane were added, followed by placing the resultant under a nitrogen atmosphere. The reaction mixture was heated at 70° C. for 15 hours and was left to be cooled down. Thereto, water and ethyl acetate were added to wash the mixture with water and the oil layer was recovered. The resultant crude product was passed through a silica gel column to be separated and purified using a mixed solvent of hexane-ethyl acetate, thus obtaining 1.4 g (3.2 mmol) of a compound (MC-3c) as a light yellow solid in a yield of 36%. The result of the $^1$H-NMR analysis is shown below:

$^1$H-NMR (400 MHz/CDCl$_3$): δ (ppm) 7.61-7.56 (m, 4H), 7.35 (s, 2H), 2.83 (t, 2H), 1.97 (d, 6H), 1.88 (q, 2H), 1.03 (t, 3H).

<Stage 4>

One point three (1.3) grams (3.0 mmol) of the compound (MC-3c), 1.5 g (3.3 mmol) of 3,5-di(4-tert-butylphenyl) phenylboronic acid pinacol ester, and 950 mg (9.0 mmol) of sodium carbonate were weighed, and thereto, 6 mL of water and 15 mL of dioxane were added, followed by placing the resultant under a nitrogen atmosphere. Thereto, 70 mg (0.06 mmol) of tetrakistriphenylphosphino palladium (0) was added, followed by heating and refluxing the resultant for 5 hours under a nitrogen atmosphere. After cooling down, water and toluene were added thereto to wash the resultant with water. The oil layer was recovered and then concentrated. The resultant crude product was passed through a silica gel column to be separated and purified using a mixed solvent of hexane-chloroform-ethyl acetate, thus obtaining 2.0 g (2.9 mmol) of a compound (MC-3d) as light yellow powder in a yield of 97%. The result of the $^1$H-NMR analysis is shown below:

$^1$H-NMR (400 MHz/((CD$_3$)$_2$CO): δ (ppm) 7.92 (d, 2H), 7.89 (tt, 1H), 7.77 (d, 4H), 7.74 (d, 4H), 7.70 (d, 2H), 7.53 (dt, 4H), 2.78 (t, 2H), 2.04 (s, 6H), 1.85 (td, 2H), 1.34 (s, 18H), 1.00 (t, 3H).

<Stage 5>

One hundred eighty (180) milligrams (0.5 mmol) of iridium chloride and 770 mg (1.1 mmol) of the compound (MC-3d) were weighed and thereto, 4 mL of water and 12 mL of 2-ethyloxyethanol were added, followed by heating and refluxing the resultant for 7 hours under an argon atmosphere. After cooling down, water and methanol were poured thereto. The deposited precipitate was subjected to suction filtration and then washed with methanol to obtain 900 mg of yellow powder. Then, 900 mg of the yellow powder, 1.2 g (1.7 mmol) of the compound (MC-3d), and 130 mg (0.5 mmol) of silver trifluoromethanesulfonate were weighed and thereto, 5 mL of diethylene glycol dimethyl ester was added, followed by heating and refluxing the resultant for 11 hours under an argon atmosphere. After cooling down, toluene was added thereto and the resultant was subjected to suction filtration. Water was added to the filtrate to wash the filtrate with water and the oil layer was recovered and concentrated. The crude product was dissolved in toluene and then passed through a silica gel column to be separated and purified using a mixed solvent of toluene-hexane. The eluate was concentrated and then recrystallized from a mixed solvent of diethylether-hexane, thus obtaining 760 mg (0.33 mmol) of a compound (MC-3) [fac-tris(1-(4-(3,5-di(4-tert-butylphenyl)phenyl)-2,6-dimethyl)phenyl-3-propyl-5-(4-trifluoromethylphenyl)-1H-[1,2,4]-triazolato-N,C2') iridium (III)] as yellow solid powder in a yield of 66%. The result of the $^1$H-NMR analysis is shown below:

$^1$H-NMR (400 MHz/CDCl$_3$): δ (ppm) 7.85-7.81 (m, 9H), 7.69-7.65 (m, 12H), 7.62 (s, 3H), 7.58 (s, 3H), 7.55-7.51 (m, 12H), 6.95 (dd, 3H), 6.78 (d, 3H), 6.68 (d, 3H), 2.52-2.28 (m, 15H), 1.86 (s, 9H), 1.36 (hep, 6H), 1.19 (s, 54H), 0.89 (t, 9H).

Example 4

Synthesis of Compound (MC-4)

[Chem. 26]

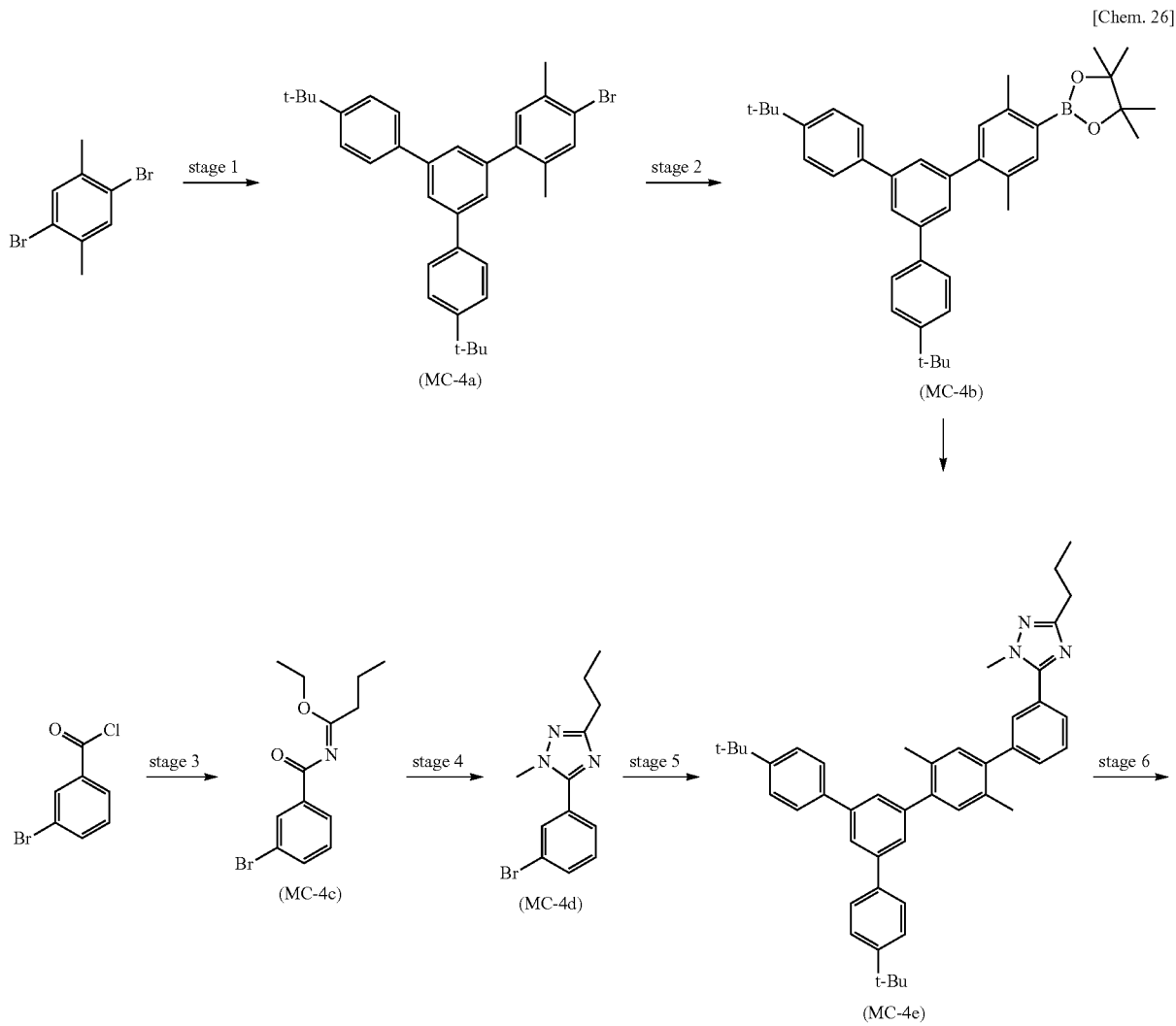

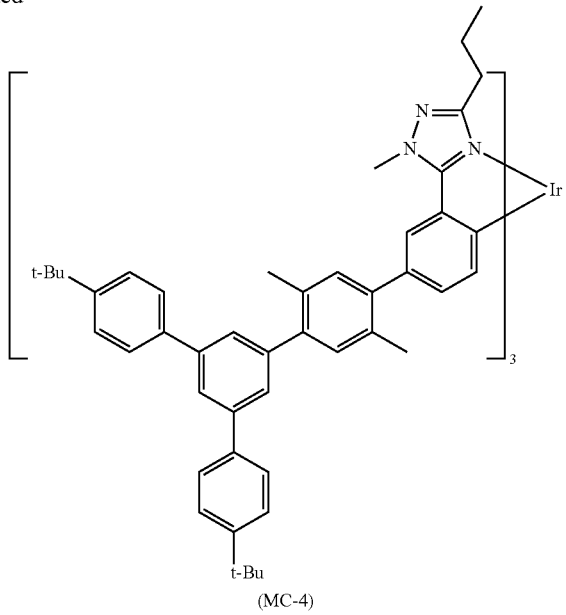

(MC-4)

<Stage 1>

Five point two eight (5.28) grams (20 mmol) of 2,5-dibromoxylene and 9.36 g (20 mmol) of 3,5-di(4-tert-butylphenyl)phenylboronic acid pinacol ester were weighed and thereto, 30 g (40 mmol) of tetraethylammonium hydroxide was added, and then, 920 mg (0.8 mmol) of tetrakistriphenylphosphino palladium (0) and 100 mL of dioxane were added. The resultant was bubbled with nitrogen. Thereafter, the resultant was heated at 80° C. for 4 hours. After cooling down, the reaction liquid was passed through a Celite layer and then concentrated. Water and toluene were added to the obtained oily substance and the resultant was transferred into a separating funnel and washed with water. The resultant oil layer was dried over anhydrous sodium sulfate and then concentrated. The obtained light yellow oil was dissolved in hexane-toluene (hexane:toluene=9:1 in terms of a volume ratio), and then passed through a silica gel column to be purified, thus obtaining 6.0 g (10.5 mmol) of a compound (MC-4-a) as a powdered white solid in a yield of 52%. The result of the $^1$H-NMR analysis is shown below:

$^1$H-NMR (400 MHz/CDCl$_3$): δ (ppm) 7.78 (t, 1H), 7.60 (ddd, 4H), 7.49 (m, 5H), 7.46 (d, 2H), 7.20 (s, 1H), 2.40 (s, 3H), 2.29 (s, 3H), 1.37 (s, 18H).

<Stage 2>

Five point two seven (5.27) grams (10 mmol) of the compound (MC-4-a), 3.81 g (15 mmol) of bis(pinacolato) diboron, and 163 mg (0.2 mmol) of dichlorobis(diphenylphosphino)ferrocenyl palladium (II) dichloromethane complex, and 2.94 g (30 mmol) of potassium acetate were weighed, and thereto, 50 mL of dioxane was poured, followed by bubbling the resultant with nitrogen for 15 minutes. Thereafter, the resultant was heated and refluxed under a nitrogen atmosphere for 5 hours. After cooling down, the resultant was passed through a Celite layer, and filtered, followed by concentrating the filtrate. The obtained residue was dissolved in a mixed solvent of hexane-toluene (hexane:toluene=7:3 in terms of a volume ratio), and then passed through a silica gel column to be purified, thus obtaining 5.39 g (9.4 mmol) of a compound (MC-4-b) as a powdered white solid in a yield of 94%. The result of the $^1$H-NMR analysis is shown below:

$^1$H-NMR (400 MHz/CDCl$_3$): δ (ppm) 7.77 (t, 1H), 7.72 (s, 1H), 7.61 (d, 4H), 7.50-7.47 (m, 6H), 7.17 (s, 1H), 2.55 (s, 3H), 2.33 (s, 3H), 1.37 (s, 18H), 1.26 (s, 12H).

<Stage 3>

Six point nine two (6.92) grams (31.5 mmol) of 3-bromobenzoyl chloride and 4.95 g (32.6 mmol) of butyrimide acid hydrochloride were weighed and were dissolved in 150 mL out of 300 mL of chloroform, and the resultant was placed under a nitrogen atmosphere. Thereafter, 30 mL of a chloroform solution of 8 mL (60 mmol) of triethylamine was added dropwise thereto and the resultant was stirred under a nitrogen atmosphere at room temperature. After 15 hours, chloroform as a solvent was concentrated and the concentrate was suspended in 200 mL of water, followed by extracting the resultant with dichloromethane. After drying over anhydrous sodium sulfate, the oil layer was concentrated, thus obtaining 9.47 g of a compound (MC-4-c) as a colorless liquid in a yield of 100%. The result of the $^1$H-NMR analysis is shown below:

$^1$H-NMR (400 MHz/CDCl$_3$): δ (ppm) 8.14 (t, 1H), 7.93 (dd, 1H), 7.65-7.63 (m, 1H), 7.31 (t, 1H), 4.29 (q, 2H), 2.36 (t, 2H), 1.60 (td, 2H), 1.37 (t, 3H), 0.88 (t, 3H).

<Stage 4>

In a dropping funnel, 1.52 g (33 mmol) of anhydrous methylhydrazine and 15 mL of dehydrated chloroform were placed, and thereto, 594 mg of water was added, followed by bubbling with argon to prepare a methylhydrazine solution. Then, 9.0 g of the compound (MC-4-c) was dissolved in 100 mL of chloroform and thereto, the methylhydrazine solution was added dropwise under an argon atmosphere. After the completion of dropwise addition, the resultant was stirred at room temperature for 7 hours under an argon atmosphere. To the resultant solution, 100 mL of water was poured to quench the reaction and then the oil layer was recovered and concentrated. Thereafter, the resultant was passed through a silica gel column to remove hydrazine. Then, the obtained solution was passed through a silica gel column to be separated and purified using an eluent of dichloromethane-ethyl acetate (dichloromethane:ethyl acetate=7:3 in terms of a volume ratio), thus obtaining 5.8 g of a compound (MC-4-d) in a yield of 63%. The result of the $^1$H-NMR analysis is shown below:

$^1$H-NMR (400 MHz/CDCl$_3$): δ (ppm) 7.85 (d, 1H), 7.63-7.57 (m, 2H), 7.37 (1H, dd), 3.93 (s, 3H), 2.72 (t, 2H), 1.81 (m, 2H), 1.01 (t, 3H).

<Stage 5>

One point one two (1.12) grams (4 mmol) of the compound (MC-4-d), 2.29 g (4 mmol) of the compound (MC-4-b), 46 mg (0.04 mmol) of tetrakistriphenylphosphino palladium (0), and 1.27 g (12 mmol) of sodium carbonate were weighed and thereto, 10 mL of water and 20 mL of THF were added, followed by heating and refluxing the resultant for 4 hours under a nitrogen atmosphere. After cooling down, the reaction liquid was concentrated, and thereto, water and toluene were added to wash the concentrate. The oil layer was dried over magnesium sulfate and then concentrated, followed by dissolving the concentrate in a mixed solvent of chloroform-ethyl acetate (chloroform:ethyl acetate=10:1 in terms of a volume ratio). The resultant was passed through a silica gel column to be separated and purified, thus obtaining 2.0 g (3.1 mmol) of a compound (MC-4-e) as powdered white solid in a yield of 77%. The result of the $^1$H-NMR analysis is shown below:

$^1$H-NMR (400 MHz/CDCl$_3$): δ (ppm) 7.80 (t, 1H), 7.67-7.62 (m, 6H), 7.59-7.54 (m, 3H), 7.52 (t, 1H), 7.49 (ddd, 4H), 7.28 (s, 1H), 7.21 (s, 1H), 3.97 (s, 3H), 2.74 (t, 2H), 2.37 (s, 3H), 2.30 (s, 3H), 1.83 (dt, 2H), 1.38 (s, 18H), 1.03 (t, 3H).

<Stage 6>

One hundred seventy six (176) milligrams (0.5 mmol) of iridium chloride hydrate and 710 mg (1.1 mmol) of the compound (MC-4-e) were weighed and placed into 30 mL of three-necked flask, and thereto, 4 mL of water and 12 mL of 2-ethoxyethanol were added. The resultant was heated and refluxed under an argon atmosphere for 7 hours. Thereafter, water and methanol were added thereto and a deposited precipitate was subjected to suction filtration. Then, 850 mg of the obtained yellow powder, 1.25 g (1.9 mmol) of the compound (MC-4-e), and 130 mg (0.5 mmol) of silver trifluoromethanesulfonate were weighed, and thereto, 6 mL of diethylene glycol dimethyl ester was added, followed by heating and refluxing the resultant for 8 hours under a nitrogen atmosphere. After cooling down, toluene was added thereto and the resultant was passed through a Celite layer to be filtered. The filtrate was concentrated, and then, the residue was dissolved in a mixed solvent of hexane-toluene-ethyl acetate (hexane:toluene:ethyl acetate=3:2:1 in terms of a volume ratio), and the resultant was passed through a silica gel column to be separated and purified, thus obtaining 680 mg (0.32 mmol) of a compound (MC-4) as a powdered light yellow solid in a yield of 64%. The result of the $^1$H-NMR analysis is shown below:

$^1$H-NMR (400 MHz/CDCl$_3$): δ (ppm) 7.79 (t, 3H), 7.64 (ddd, 12H), 7.58 (d, 3H), 7.56 (s, 6H), 7.50 (ddd, 12H), 7.26 (d, 6H), 6.90 (dd, 3H), 6.82 (d, 3H), 4.22 (s, 9H), 2.37 (s, 9H), 2.35 (s, 9H), 2.28 (ddd, 3H), 1.95 (ddd, 3H), 1.44-1.39 (m, 3H), 1.36 (s, 54H), 1.31-1.18 (m, 3H), 0.73 (t, 9H)

Comparative Example 1

Synthesis of Compound (MC-5)

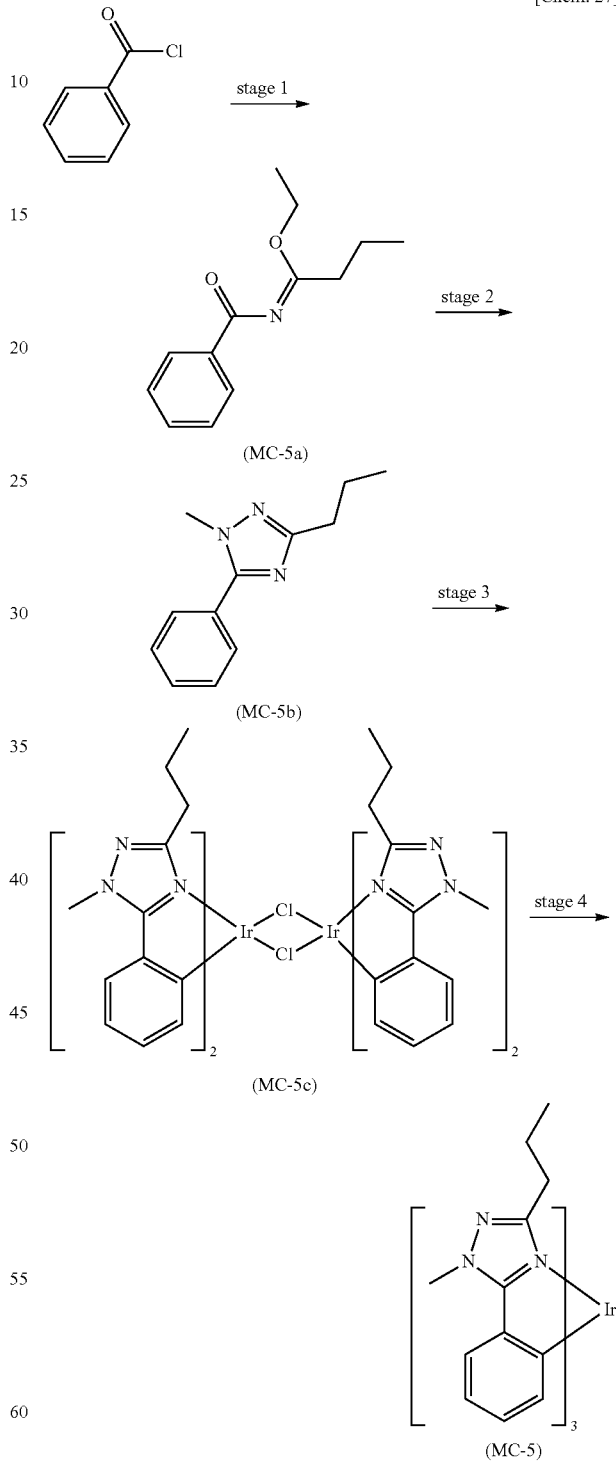

<Stage 1>

Three (3) milliliters (26 mmol) of benzoyl chloride and 3.9 g (26 mmol) of ethyl butyrimidate hydrochloride were weighed and were dissolved in 300 mL of chloroform, and the resultant was placed under a nitrogen atmosphere. Thereafter, 25 mL of a chloroform solution of 7.2 mL (52 mmol) of triethylamine was added dropwise thereto and the resultant was stirred under a nitrogen atmosphere at room temperature. After 15 hours, chloroform as a solvent was concentrated and the concentrate was suspended in 200 mL of water, followed by extracting the resultant with dichloromethane. The obtained solution was concentrated under reduced pressure, thus obtaining 5.3 g (24 mmol) of a compound (MC-5a) as a light yellow liquid.

<Stage 2>

5.3 g (24 mmol) of the compound (MC-5a) was dissolved in 200 mL of chloroform and the resultant was placed under a nitrogen atmosphere. Thereto, 25 mL of a chloroform solution containing 1.2 mL (26 mmol) of methylhydrazine and 0.5 mL of water was added dropwise under a nitrogen atmosphere at room temperature. After the dropwise addition, the resultant was stirred for 15 hours under a nitrogen atmosphere at room temperature and then 100 mL of water was added thereto to quench the reaction. Thereafter, the reaction liquid was transferred into a separating funnel and was washed with water, followed by recovering and concentrating an oil layer. The crude product was passed through a silica gel column to be purified using a mixed solvent of dichloromethane-ethyl acetate. The eluate was concentrated, thus obtaining 2.9 g of a compound (MC-5b) as a colorless liquid in a yield of 60%. The result of the $^1$H-NMR analysis is shown below:

$^1$H-NMR (400 MHz/CDCl$_3$): δ (ppm) 7.75 (m, 3H), 7.66 (m, 2H), 3.93 (s, 3H), 2.73 (t, 2H), 1.82 (hex, 2H), 1.02 (t, 3H).

<Stage 3>

Three hundred fifty (350) milligrams (1.0 mmol) of iridium chloride and 440 mg (2.2 mmol) of the compound (MC-5b) were weighed and thereto, 10 mL of 2-ethyloxyethanol and 5 mL of water were added. The resultant was placed under a nitrogen atmosphere and was heated and refluxed for 15 hours. After cooling down, the reaction liquid was concentrated. To the residue, water and dichloromethane were added to wash the oil layer with water. The oil layer was recovered, concentrated, and dried, thus obtaining 660 mg of a compound (MC-5c) as a yellow oily substance.

<Stage 4>

One point zero (1.0) grams (5.0 mmol) of the compound (MC-5c) and the compound (MC-5c) were weighed, and thereto, 260 mg of silver trifluoromethanesulfonate was added, followed by replacing the atmosphere in the reaction system with argon. The resultant was heated to react at 165° C. for 15 hours and was left to be cooled down, and thereto, 15 mL of dichloromethane was poured. The suspension was subjected to suction filtration and then passed through a silica gel column to be separated and purified using a mixed solvent of dichloromethane-ethyl acetate, thus obtaining 630 mg of a compound (MC-5) [fac-tris(1-methyl-3-propyl-5-phenyl-1H-[1,2,4]-triazolato-N,C2') iridium (III)] as a yellow powder in a yield of 80%. The result of the $^1$H-NMR analysis is shown below:

$^1$H-NMR (400 MHz/CDCl$_3$): δ (ppm) 7.50 (d, 3H), 6.88 (t, 3H), 6.80 (t, 3H), 6.63 (d, 3H), 4.11 (s, 9H), 2.18 (hep, 3H), 1.87 (hep, 3H), 1.38-1.30 (m, 3H), 1.18-1.10 (m, 3H), 0.68 (t, 9H).

Test Example 1

Evaluation of Stability of Compound MC-1

A liquid composition 1 was prepared by mixing a solution in which 2.2% by weight of polystyrene manufactured by Fluka Ltd. (weight average molecular weight Mw=600000) was dissolved in a xylene solvent and a solution in which 2.2% by weight of the compound MC-1 was dissolved in a xylene solvent so that the polystyrene solution and the solution of the compound MC-1 are mixed in 70% by weight and 30% by weight, respectively.

Onto a glass substrate having an ITO film of thickness of 45 nm provided thereon by a sputtering method, the liquid composition 1 was applied by a spin coating method to form a film in thickness of 100 nm. The resultant was dried at 130° C. for 10 minutes under a nitrogen atmosphere having an oxygen concentration and a moisture concentration of each 10 ppm or less (based on weight). Thereonto, aluminum was vapor deposited in a thickness of about 80 nm as a cathode. After the vapor deposition of aluminum, by sealing with a glass substrate, a light-emitting device 1 was manufactured. The vapor deposition of the metal was initiated after a degree of vacuum reached 1×10$^{-4}$ Pa or less.

The obtained light-emitting device 1 was irradiated with ultraviolet in an excitation wavelength of 325 nm using He—Cd laser, and a light-emission luminance was measured with BM-9 manufactured by TOPCON TECHNOHOUSE CORPORATION. An intensity of the excitation light was set to 1.8 mW (irradiation area was about 4 mm$^2$). When the above ultraviolet irradiation was carried out on the light-emitting device 1, the light-emitting device 1 initially emitted light at 477 cd/m$^2$ and a time that the light-emission luminance was decreased by 30% was 71.6 hours. Therefore, a luminance half-lifetime of the light-emitting device 1 is longer than 71.6 hours.

Test Example 2

Evaluation of Stability of Compound MC-2

A liquid composition 2 was prepared by mixing a solution in which 2.2% by weight of polystyrene manufactured by Fluka Ltd. (weight average molecular weight Mw=600000) was dissolved in a xylene solvent and a solution in which 2.2% by weight of the compound MC-2 was dissolved in a xylene solvent so that the polystyrene solution and the solution of the compound MC-2 are mixed in 70% by weight and 30% by weight, respectively.

A light-emitting device 2 was manufactured in the same manner as Test Example 1, except that the liquid composition 2 was used instead of the liquid composition 1 in Test Example 1.

When an ultraviolet irradiation was carried out on the light-emitting device 2 in the same manner as Test Example 1, the light-emitting device 2 initially emitted light at 456 cd/m$^2$ and had a luminance half-lifetime of 27.3 hours.

Test Example 3

Evaluation of Stability of Compound MC-3

A liquid composition 3 was prepared by mixing a solution in which 2.2% by weight of polystyrene manufactured by Fluka Ltd. (weight average molecular weight Mw=600000) was dissolved in a xylene solvent and a solution in which 2.2% by weight of the compound MC-3 was dissolved in a xylene solvent so that the polystyrene solution and the solution of the compound MC-3 are mixed in 70% by weight and 30% by weight, respectively.

A light-emitting device 3 was manufactured in the same manner as Test Example 1, except that the liquid composition 3 was used instead of the liquid composition 1 in Test Example 1.

When an ultraviolet irradiation was carried out on the light-emitting device 3 in the same manner as Test Example 1, the light-emitting device 3 initially emitted light at 730 cd/m² and had a luminance half-lifetime of 37.9 hours.

Test Example 4

Evaluation of Stability of Compound MC-4

A liquid composition 4 was prepared by mixing a solution in which 2.2% by weight of polystyrene manufactured by Fluka Ltd. (weight average molecular weight Mw=600000) was dissolved in a xylene solvent and a solution in which 2.2% by weight of the compound MC-4 was dissolved in a xylene solvent so that the polystyrene solution and the solution of the compound MC-4 are mixed in 70% by weight and 30% by weight, respectively.

A light-emitting device 4 was manufactured in the same manner as Test Example 1, except that the liquid composition 4 was used instead of the liquid composition 1 in Test Example 1.

When an ultraviolet irradiation was carried out on the light-emitting device 4 in the same manner as Test Example 1, the light-emitting device 4 initially emitted light at 1571.5 cd/m² and had a luminance half-lifetime of 8.3 hours.

Test Comparative Example 1

Evaluation of Stability of Compound MC-5

A liquid composition 5 was prepared by mixing a solution in which 2.2% by weight of polystyrene manufactured by Fluka Ltd. (weight average molecular weight Mw=600000) was dissolved in a xylene solvent and a solution in which 2.2% by weight of the compound MC-5 was dissolved in a xylene solvent so that the polystyrene solution and the solution of the compound MC-5 are mixed in 70% by weight and 30% by weight, respectively.

A light-emitting device 5 was manufactured in the same manner as Test Example 1, except that the liquid composition 5 was used instead of the liquid composition 1 in Test Example 1.

When an ultraviolet irradiation was carried out on the light-emitting device 5 in the same manner as Test Example 1, the light-emitting device 5 initially emitted light at 686.5 cd/m² and had a luminance half-lifetime of 0.79 hours.

The results of the stability tests are shown in Table 1. The results of the stability tests demonstrated that the metal complex of the present invention had excellent stability and was useful for the material for the light-emitting device.

<Measurement of Emission Spectrum at Room Temperature>

The compounds MC-1 to MC-5 were each dissolved in THF (manufactured by KANTO CHEMICAL CO., INC.: grade for spectroscopy) so as to have a concentration of $1\times10^6$ mol/L. Argon gas was passed therethrough, followed by measuring an emission spectrum at room temperature (excitation wavelength: 350 nm) using an absolute PL quantum yield measurement system (C9920) manufactured by Hamamatsu Photonics K.K.

<Measurement of Emission Spectrum at 77 K>

The compounds MC-1 to MC-5 were each dissolved in 2-MeTHF (manufactured by Sigma-Aldrich Co. LLC.: anhydrous, inhibitor-free) so as to have a concentration of $1\times10^{-6}$ mol/L. Argon gas was passed therethrough, followed by measuring an emission spectrum at 77 K (excitation wavelength: 350 nm) using the absolute PL quantum yield measurement system (C9920) manufactured by Hamamatsu Photonics K.K.

Table 1 lists emission wavelengths obtained from the results of the emission spectra at room temperature and the emission spectra at 77 K. The results of the emission spectrum measurement demonstrated that the metal complex of the present invention emitted light in a blue region.

The invention claimed is:
1. A metal complex represented by Formula (1):

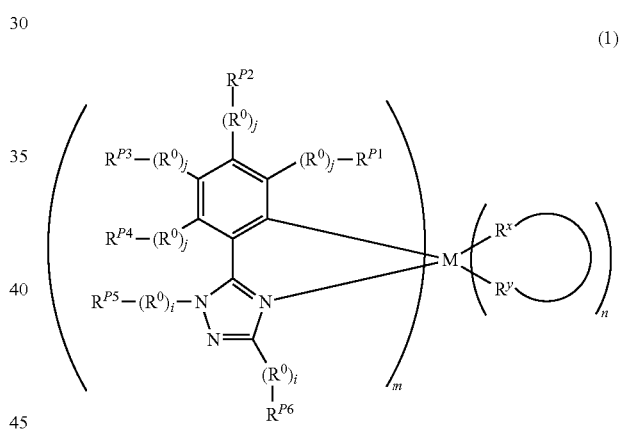

wherein
M is a metal atom selected from the group consisting of a ruthenium atom, a rhodium atom, a palladium atom, an osmium atom, an iridium atom and a platinum atom;

TABLE 1

|  | Compound | luminance half-lifetime in ultraviolet irradiation (hr) | Peak wavelength of emission spectrum @77 K (nm) | Peak wavelength of emission spectrum @RT (nm) |
| --- | --- | --- | --- | --- |
| Test Example 1 | MC-1 | 71.6 (luminance 70%) | 477 | 495 |
| Test Example 2 | MC-2 | 27.3 | 450 | 459 |
| Test Example 3 | MC-3 | 37.9 | 465 | 471 |
| Test Example 4 | MC-4 | 8.3 | 454 | 461 |
| Test Comparative Example 1 | MC-5 | 0.79 | 443 | 453 | each $R^0$ is a group represented by Formula (L-2):

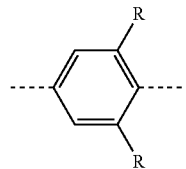

(L-2)

wherein each R independently represents an alkyl group;
each i independently represents 0 or 1;
each j independently represents 0 or 1;
$R^{P1}$, $R^{P2}$, $R^{P3}$, $R^{P4}$ and $R^{P5}$ each independently represent a hydrogen atom, a halogen atom, an alkyl group, an alkyloxy group, an alkylthio group, an aryl group, an aryloxy group, an arylthio group, an arylalkyl group, an arylalkyloxy group, an arylalkylthio group, an acyl group, an acyloxy group, a carbamoyl group, an amido group, an acid imido group, an imine residue, a substituted amino group, a substituted silyl group, a substituted silyloxy group, a substituted silylthio group, a substituted silylamino group, a monovalent heterocyclic group, a heteroaryloxy group, a heteroarylthio group, an arylalkenyl group, an arylalkynyl group, a substituted carboxyl group or a cyano group, $R^{P6}$ represents a halogen atom, an alkyl group, an alkyloxy group, an aryl group or a monovalent heterocyclic group, and $R^{P1}$ and $R^{P2}$ may be connected to form a ring structure, $R^{P2}$ and $R^{P3}$ may be connected to form a ring structure, and $R^{P3}$ and $R^{P4}$ may be connected to form a ring structure, with a proviso that at least one of $R^{P1}$, $R^{P2}$, $R^{P3}$, and $R^{P4}$ is a dendron, j which represents the number of the linking group $R^0$ linking to the dendron is 1;
m is an integer of from 1 to 3, n is an integer of from 0 to 2, and m+n is 2 or 3;
the portion represented by Formula (2):

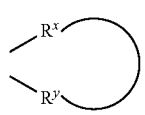

(2)

represents a bidentate ligand;
wherein $R^x$ and $R^y$ are an atom bonding to the metal atom M, and each independently represent a carbon atom, an oxygen atom or a nitrogen atom.

2. The metal complex according to claim 1, wherein n is 0.

3. The metal complex according to claim 1, wherein at least one of $R^{P1}$, $R^{P2}$, $R^{P3}$ and $R^{P4}$ is an electron-acceptor substituent.

4. The metal complex according to claim 3, wherein the electron-acceptor substituent is a fluorine atom or a substituent containing a fluorine atom.

5. The metal complex according to claim 1, which is represented by Formula (3-2):

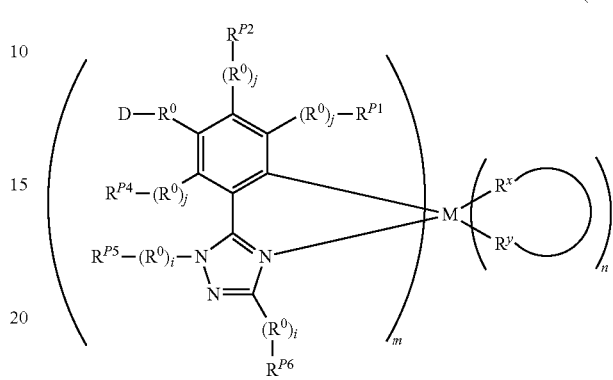

(3-2)

wherein M, $R^0$, $R^{P1}$, $R^{P2}$, $R^{P4}$, $R^{P5}$, $R^{P6}$, the portion represented by Formula (2), $R^x$, $R^y$, i, j, m and n represent the same meaning as above, and D represents the dendron.

6. The metal complex according to claim 1, wherein M is a platinum atom or an iridium atom.

7. The metal complex according to claim 1, wherein a peak wavelength of an emission spectrum of a dilute solution of the metal complex is from 430 nm to 630 nm, wherein the dilute solution contains the metal complex in an organic solvent at a concentration of from $1\times10^{-6}$ to $1\times10^{-7}$ mol/L, and wherein the emission spectrum is a PL spectrum measured at room temperature.

8. A composition comprising:
  (a) the metal complex according to claim 1; and
  (b) a charge transport compound.

9. The composition according to claim 8, wherein the charge transport compound is a polymer compound.

10. A composition comprising:
  (a) the metal complex according to claim 1; and
  (b) a solvent or dispersion medium.

11. A film comprising the metal complex according to claim 1.

12. A light-emitting device including:
  (a) electrodes composed of an anode and a cathode; and
  (b) a layer comprising the metal complex according to claim 1, which is provided between the electrodes.

13. A planar light source including the light-emitting device according to claim 12.

14. An illumination apparatus including the light-emitting device according to claim 12.

* * * * *

UNITED STATES PATENT AND TRADEMARK OFFICE
CERTIFICATE OF CORRECTION

PATENT NO. : 9,705,097 B2  
APPLICATION NO. : 14/372033  
DATED : July 11, 2017  
INVENTOR(S) : Nobuhiko Akino et al.

Page 1 of 1

It is certified that error appears in the above-identified patent and that said Letters Patent is hereby corrected as shown below:

On the Title Page

Item (73) Assignee should read:
SUMITOMO CHEMICAL COMPANY, LIMITED, Tokyo (JP); NATIONAL INSTITUTE OF ADVANCED INDUSTRIAL SCIENCE AND TECHNOLOGY, Tokyo (JP)

Signed and Sealed this  
Seventh Day of November, 2017

Joseph Matal  
*Performing the Functions and Duties of the  
Under Secretary of Commerce for Intellectual Property and  
Director of the United States Patent and Trademark Office*